(12) United States Patent
Kley et al.

(10) Patent No.: US 8,614,238 B2
(45) Date of Patent: Dec. 24, 2013

(54) CYCLOPENTANECARBOXAMIDE DERIVATIVES, MEDICAMENTS CONTAINING SUCH COMPOUNDS AND THEIR USE

(75) Inventors: Joerg Kley, Mittelbiberach (DE); Bradford S. Hamilton, Biberach an der Riss (DE); Juergen Mack, Biberach an der Riss (DE); Norbert Redemann, Biberach an der Riss (DE); Corinna Schoelch, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/500,924

(22) PCT Filed: Oct. 15, 2010

(86) PCT No.: PCT/EP2010/065500
§ 371 (c)(1),
(2), (4) Date: Jun. 25, 2012

(87) PCT Pub. No.: WO2011/048018
PCT Pub. Date: Apr. 28, 2011

(65) Prior Publication Data
US 2013/0053412 A1 Feb. 28, 2013

(30) Foreign Application Priority Data
Oct. 19, 2009 (EP) ..................... 09173383

(51) Int. Cl.
A61K 31/423 (2006.01)
A61K 31/167 (2006.01)
C07D 263/57 (2006.01)
C07C 237/24 (2006.01)

(52) U.S. Cl.
USPC ............ 514/375; 514/616; 548/224; 564/157

(58) Field of Classification Search
None
See application file for complete search history.

(56) References Cited

U.S. PATENT DOCUMENTS

2006/0142585 A1 6/2006 Thomas et al.
2007/0049587 A1 3/2007 Zbinden et al.

FOREIGN PATENT DOCUMENTS

WO 0230874 A2 4/2002

OTHER PUBLICATIONS

Medline Plus. "Autoimmune disorders," National Institutes of Health. <http://www.nlm.nih.gov/medlineplus/ency/article/000816. htm> Accessed Jun. 3, 2011.*
Wang et al., J. Immunol. 2007, 179, pp. 5958-5965.*
International Search Report Form PCT/ISA/210 and Written Opinion Form PCT/ISA/237 for corresponding PCT/EP2010/065500; date of mailing: Mar. 8, 2011.

* cited by examiner

Primary Examiner — Alicia L Otton
(74) Attorney, Agent, or Firm — Michael P. Morris; Alan R. Stempel

(57) ABSTRACT

The invention relates to cyclopentanecarboxamide derivatives of formula 1, to their use as Fatty Acid Synthase inhibitors, to methods for their therapeutic use and to pharmaceutical compositions containing them, wherein $R^1$, $R^2$, $R^3$, LO, W, $AR^1$, n are as defined in claim 1.

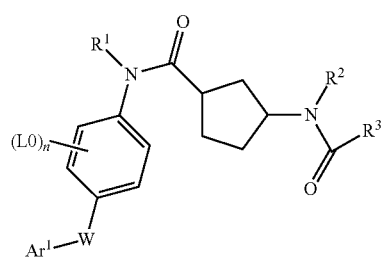

(1)

10 Claims, No Drawings

CYCLOPENTANECARBOXAMIDE DERIVATIVES, MEDICAMENTS CONTAINING SUCH COMPOUNDS AND THEIR USE

TECHNICAL FIELD OF THE INVENTION

The invention relates to cyclopentanecarboxamide derivatives, to processes for preparing such compounds, to their use as Fatty Acid Synthase inhibitors, to methods for their therapeutic use and to pharmaceutical compositions comprising them.

BACKGROUND OF THE INVENTION

Obesity and diabetes are reaching epidemic proportions in the USA, EU, Japan and developing countries. Obesity is the major driver of the co-morbidities of the metabolic syndrome, particularly type 2 diabetes.

Since no effective pharmacotherapies for obesity are available to date and current diabetes therapies do not stop the progression of the disease, there is a huge unmet medical need.

Fatty Acid Synthase (FAS) is a critical enzyme for endogenous lipogenesis and plays an important role in the modulation of key intermediates of lipid and carbohydrate cellular metabolism. FAS is highly expressed in the tissues with high metabolic activity (for example liver, adipose tissue and brain) and there are good reasons to believe that a FAS inhibitor would cause beneficial metabolic effects in peripheral tissues. In addition, inhibition of FAS in the hypothalamus may result in reduced food intake. The non-specific irreversible FAS inhibitors cerulenin and C-75 have been reported in the literature to decrease brain levels of orexigenic neuropeptides and to decrease food intake.

FAS is also highly expressed in human sebocytes, the lipid producing cells of the sebaceous glands. Acne is the most common disorder involving the sebaceous gland. The pathogenesis of acne involves lipid (over)production by the sebaceous gland and it has been reported that inhibitors of mammalian FAS inhibit the production of sebum in sebocytes (US 2005/0053631). Acne cannot occur without sebum lipids. There is an unmet medical need in the treatment of acne for agents that reduce sebum production.

Since fatty acid synthesis in bacteria is essential for cell survival, bacterial FAS (type II synthase) has emerged as a potential target for antibacterial therapy. Unlike in most other prokaryotes, fatty acid synthase activity in mycobacteria is carried out by a single high-molecular-weight, multifunctional peptide chain (type I synthase) related to mammalian FAS. Mycobacterial type I FAS has been described as a potential target for antimycobacterial therapy, e.g. the treatment of tuberculosis. With one-third of the world's population being infected with the tuberculosis *bacillus*, and multidrug-resistant strains of *Mycobacterium tuberculosis* developing, there is a high medical need for novel tuberculosis therapies. (Silvana C. Ngo, et al.: Inhibition of isolated *Mycobacterium tuberculosis* Fatty Acid Synthase I by Pyrazinamide Analogs; Antimicrobial agents and Chemotherapy 51, 7 (2007) 2430-2435)

Recently, microdomains of organelle membranes rich in sphingomyelin and cholesterol (called "lipid rafts") have been considered to act as a scaffold for the hepatitis C virus (HCV) replication complex (F. Amemiya, et al.: Targeting Lipid Metabolism in the Treatment of Hepatitis C Virus Infection. The Journal of Infectious Diseases 197 (2008) 361-70). Consequently, alterations of membrane lipid composition and/or distribution may influence viral replication. Indeed, agents related to lipid metabolism like polyunsaturated fatty acids or HMG-CoA reductase inhibitors (statins) have been shown to affect the replication of genotype 1 HCV (dto). These agents may attenuate HCV replication through the destruction of lipid rafts, according to their pharmacological actions. An alternative molecular mechanism possibly responsible for the inhibition of HCV replication is via altering localization of host proteins through alterations in lipid anchoring (S. M. Sagan, et al.: The influence of cholesterol and lipid metabolism on host cell structure and hepatitis C virus replication. Biochem. Cell Biol. 84 (2006) 67-79).

Unlike polyunsaturated fatty acids, addition of saturated fatty acids or oleic acid to cultured SfiI cells promoted HCV RNA replication (S. B. Kapadia, F. V. Chisari: Hepatitis C virus RNA replication is regulated by host geranylgeranylation and fatty acids. PNAS 102 (2005) 2561-66). In line with this, it has been reported that expression of fatty acid synthase was increased in a human hepatoma cell line upon HCV infection (W. Yang, et al.: Fatty acid synthase is up-regulated during hepatitis C virus infection and regulates hepatitis C virus entry. Hepatology 48, 5 (2008) 1396-1403). Furthermore, inhibition of fatty acid biosynthesis by TOFA (an inhibitor of acetyl-CoA carboxylase) or inhibitors of fatty acid synthase (cerulenin, C75), led to decreased HCV production (dto).

The effect of fatty acid synthase (FAS) activity on viral replication or infection appears not to be restricted to HCV, but has also been reported for HIV (D. H. Nguyen, D. D. Taub: Targeting Lipids to Prevent HIV infection. Molecular Interventions 4, 6 (2004) 318-320), Poliovirus (R. Guinea, L. Carrasco: Effects of Fatty Acids on Lipid Synthesis and Viral RNA Replication in Poliovirus-Infected Cells. Virology 185 (1991) 473-476), Epstein-Barr virus (Y. Li., et al.: Fatty acid synthase expression is induced by the Epstein-Barr virus immediate-early protein BRLF1 and is required for lytic viral gene expression. Journal of Virology 78, 8 (2004) 4197-4206), human papilloma virus (L. Louw, et al.: HPV-induced recurrent laryngeal papillomatosis: fatty acid role-players. Asia Pac J Clin Nutr 17 (51) (2008) 208-211), coxsackievirus B3 (A. Rassmann, et al.: The human fatty acid synthase: A new therapeutic target for coxsackievirus B3-induced diseases? Antiviral Research 76 (2007) 150-158), Rous sarcoma virus (H. Goldfine, et al.: Effects of inhibitors of lipid synthesis on the replication of Rous Sarcoma Virus. A specific effect of cerulenin on the processing of major non-glycosylated viral structural proteins. Biochimica et Biophysica Acta 512 (1978) 229-240), as well as human cytomegalovirus (HCMV), and influenza A virus (J. Munger, et al.: Systems-level metabolic flux profiling identifies fatty acid synthesis as a target for antiviral therapy. Nature Biotechnology 26 (2008) 1179-1186).

Taken together, there is growing evidence, that activity of the host's FAS plays an important role in viral infection and viral replication, suggesting FAS as a target for antiviral therapy.

The expression of FAS is strongly increased in many cancers and there is evidence that efficient fatty acid synthesis is required for tumor cell survival. Inhibition of FAS has therefore been suggested as a new direction for oncology (Expert Opin. Investig. Drugs 16, 1 (2007)1817-1829).

AIM OF THE PRESENT INVENTION

The aim of the present invention is to provide new cyclopentanecarboxamide derivatives, particularly those which are active with regard to the enzyme Fatty Acid Synthase (FAS).

A further aim of the present invention is to provide cyclopentanecarboxamide derivatives which have an inhibitory effect on the enzyme FAS in vitro and/or in vivo and possess suitable pharmacological and pharmacokinetic properties to use them as medicaments.

A further aim of the present invention is to provide effective FAS inhibitors, in particular for the treatment or prevention of metabolic disorders, for example of obesity and/or diabetes.

A further aim of the present invention is to provide a pharmaceutical composition comprising at least one FAS inhibitor.

A further aim of the present invention is to provide a method for treating or preventing of various disorders.

Further aims of the present invention become apparent to the one skilled in the art by description hereinbefore and in the following and by the examples.

OBJECT OF THE INVENTION

Within the scope of the present invention it has now surprisingly been found that cyclopentanecarboxamide derivatives of general formula I as described hereinafter exhibit an inhibiting activity with regard to the enzyme Fatty Acid Synthase (FAS).

Therefore, in a first aspect the present invention provides a compound of formula I

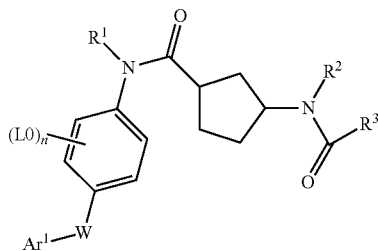

I wherein
Ar$^1$ denotes a phenyl ring or a 5- or 6-membered monocyclic heteroaryl-group which has 1 to 4 heteroatoms independently selected from the group consisting of N, O and S; and
  wherein said phenyl ring or said 5- or 6-membered monocyclic heteroaryl-group may be linked to a group Ar$^2$ via a single bond or may be condensed to a group Ar$^2$,
  wherein one or more C-atoms may be substituted independently of one another with a substituent L1; and
  wherein one or more imino-groups may be substituted independently of one another with a substituent R$^{N0}$; and
Ar$^2$ denotes a 5- or 6-membered saturated or unsaturated carbocyclic ring which may have 1 or 2 heteroatoms independently selected from the group consisting of N, O and S, or may have 3 or 4 N-atoms; and
W denotes a single bond, —C≡C—, —CH=CH—, —CH$_2$—CH$_2$— or —CH$_2$—O—;
R$^1$ denotes C$_{1-4}$-alkyl;
R$^2$ denotes H or C$_{1-4}$-alkyl;
R$^3$ denotes C$_{1-6}$-alkyl, C$_{3-6}$-alkenyl, C$_{3-6}$-alkynyl, C$_{3-6}$-cycloalkyl or R$^{N1}$R$^{N2}$N—, wherein each of said alkyl, alkenyl, alkynyl and cycloalkyl groups may be substituted with one or more substituents selected from the group consisting of R$^{N1}$R$^{N2}$N—, C$_{1-4}$-alkyl-O—C(=O)—R$^{N0}$N—, HO—, C$_{1-4}$-alkyloxy, C$_{3-7}$-cycloalkyl, phenyl and pyridinyl,
  wherein said cycloalkyl, phenyl and pyridinyl may be substituted with one or more substituents L2;
R$^{N0}$ denotes H or C$_{1-4}$-alkyl;
R$^{N1}$, R$^{N2}$ independently of each other selected from H, C$_{1-4}$-alkyl, phenyl, pyridinyl, phenyl-C$_{1-3}$-alkyl, pyridinyl-C$_{1-3}$-alkyl or R$^{N1}$, R$^{N2}$ are linked to each other to form with the N-atom of the R$^{N1}$R$^{N2}$N— group a heterocyclic ring selected from the group consisting of pyrrolidinyl, piperidinyl, morpholinyl, thiomorpholinyl, piperazinyl or 4-(C$_{1-4}$-alkyl)-piperazinyl;
L0, L1 independently of each other selected from the group consisting of F, Cl, Br, cyano, OH, C$_{1-4}$-alkyl, C$_{2-4}$-alkenyl, C$_{1-4}$-alkyloxy, C$_{1-4}$-alkylcarbonyl, R$^{N1}$R$^{N2}$N—, R$^{N1}$R$^{N2}$N—C$_{1-3}$-alkyl-, R$^{N1}$R$^{N2}$N—CO—, C$_{1-4}$-alkyl-CO—NR$^{N0}$— and C$_{1-4}$-alkyl-SO$_2$—NR$^{N0}$—, wherein alkyl-groups may be mono- or polyfluorinated;
L2 independently of each other selected from the group consisting of F, Cl, Br, cyano, OH, C$_{1-4}$-alkyl, C$_{1-4}$-alkyloxy, R$^{N1}$R$^{N2}$N—, R$^{N1}$R$^{N2}$N—C$_{1-3}$-alkyl-, wherein alkyl-groups may be mono- or polyfluorinated;
n denotes an integer from 0 to 4;
while, unless otherwise stated, the above-mentioned alkyl groups may be straight-chain or branched,
the tautomers, the stereoisomers thereof, the mixtures thereof and the salts thereof.

In a further aspect the present invention relates to processes for preparing a compound of general formula I and to the new intermediate compounds in these processes, or salts thereof.

A further aspect of the invention relates to the salts of the compounds of general formula I according to this invention, in particular to the physiologically acceptable salts.

In a further aspect this invention relates to pharmaceutical compositions, comprising one or more compounds of general formula I or one or more physiologically acceptable salts thereof according to the invention, optionally together with one or more inert carriers and/or diluents.

In a further aspect this invention relates to a method for treating or preventing diseases or conditions which can be influenced by inhibiting the activity with regard to the enzyme Fatty Acid Synthase (FAS) in a patient in need thereof characterized in that a compound of general formula I or a salt thereof is administered to the patient.

According to another aspect of the invention, there is provided a method for treating or preventing obesity, overweight, weight gain or eating disorders in a patient in need thereof characterized in that a compound of general formula I or a salt thereof is administered to the patient.

According to another aspect of the invention, there is provided a method for modulating appetite and/or satiety in a patient in need thereof characterized in that a compound of general formula I or a salt thereof is administered to the patient.

According to another aspect of the invention, there is provided a method for treating or preventing metabolic disorders and/or complications associated with metabolic disorders in a patient in need thereof characterized in that a compound of general formula I or a salt thereof is administered to the patient.

According to another aspect of the invention, there is provided a method for treating or preventing cardiovascular disorders in a patient in need thereof characterized in that a compound of general formula I or a salt thereof is administered to the patient.

According to another aspect of the invention, there is provided a method for treating or preventing inflammatory disorders in a patient in need thereof characterized in that a compound of general formula I or a salt thereof is administered to the patient.

According to another aspect of the invention, there is provided a method for treating or preventing neurodegenerative disorders in a patient in need thereof characterized in that a compound of general formula I or a salt thereof is administered to the patient.

According to another aspect of the invention, there is provided a method for treating or preventing diseases of the sebaceous gland and/or for decreasing sebum production in sebaceous glands in a patient in need thereof characterized in that a compound of general formula I or a salt thereof is administered to the patient.

According to another aspect of the invention, there is provided a method for treating or preventing mycobacterial infections in a patient in need thereof characterized in that a compound of general formula I or a salt thereof is administered to the patient.

According to another aspect of the invention, there is provided a method for treating or preventing viral infections in a patient in need thereof characterized in that a compound of general formula I or a salt thereof is administered to the patient.

According to another aspect of the invention, there is provided a method for treating or preventing cancer in a patient in need thereof characterized in that a compound of general formula I or a salt thereof is administered to the patient.

According to another aspect of the invention, there is provided the use of a compound of the general formula I or a physiologically acceptable salt thereof for the manufacture of a medicament for a therapeutic and/or preventive method as described hereinbefore and hereinafter.

According to another aspect of the invention, there is provided a compound of the general formula I or a physiologically acceptable salt thereof for a therapeutic and/or preventive method as described hereinbefore and hereinafter.

Other aspects of the invention become apparent to the one skilled in the art from the specification and the experimental part as described hereinbefore and hereinafter.

DETAILED DESCRIPTION

The compounds according to the formula I exhibit a disubstituted cyclopentane ring. Thus the compounds according to the invention have two chiral centers at the cyclopentane ring, so that the stereoisomers RS, SR, RR and RR may be distinguished. The compounds according to the invention may exhibit one or more further chiral groups. The compounds according to the invention may exist as a mixture of two or more of the above mentioned stereoisomers. Compounds of different diastereomeric forms, including racemates, may be separated and, if needed, purified by methods known in the art.

According to one embodiment compounds of the present invention are described by the formula I-RS:

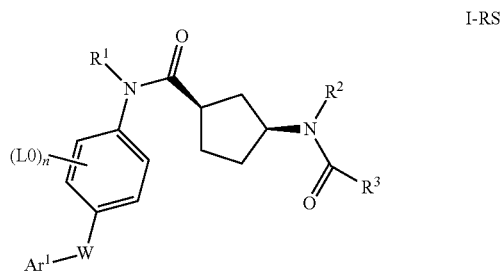

I-RS

According to another embodiment compounds of the present invention are described by the formula I-RR:

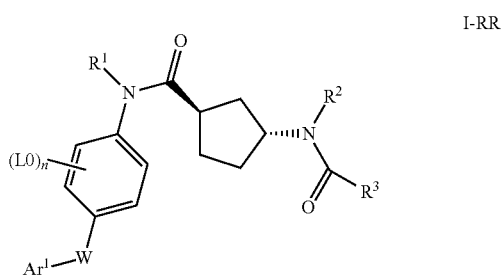

I-RR

According to still another embodiment compounds of the present invention are described by the formula I-SS:

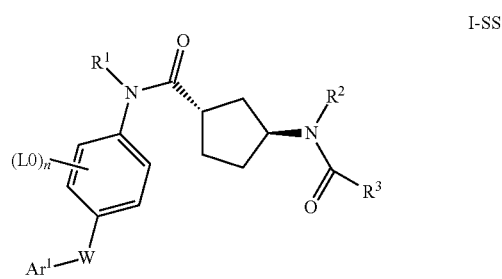

I-SS

According to still another embodiment compounds of the present invention are described by the formula I-SR:

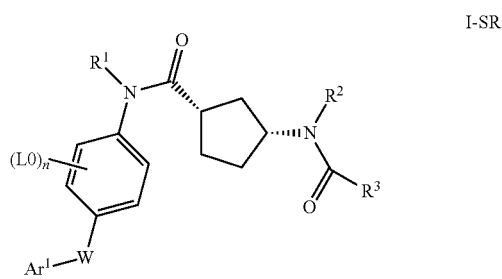

I-SR

According to one aspect the invention refers to a mixture of compounds of the formula I-RS and I-SR. The mixture may be a racemic mixture. Preferably the mixture comprises more than 50% by weight of compounds of the formula I-RS. Even more preferably the mixture comprises more than 80% by weight of compounds of the formula I-RS.

According to another aspect the invention refers to a mixture of compounds of the formula I-RR and I-SS.

Unless otherwise stated, the groups, residues, and substituents, particularly $Ar^1$, $Ar^2$, W, $R^1$, $R^2$, $R^3$, $R^{N0}$, $R^{N1}$, $R^{N2}$, L0, L1, L2 and the index n are defined as above and hereinafter. If residues, substituents, or groups occur several times in a compound, as for example L0, L1 or L2, they may have the same or different meanings. Some preferred meanings of individual groups and substituents of the compounds according to the invention will be given hereinafter.

$Ar^1$:

$Ar^1$-A1: In one embodiment the group $Ar^1$ preferably denotes phenyl, thienyl, pyridinyl, pyrrolyl, imidazolyl, triazolyl, furanyl or oxazolyl.

$Ar^1$-A2: In this embodiment the group $Ar^1$ even more preferably denotes phenyl, thienyl or pyridinyl.

$Ar^1$-B1: In another embodiment the group $Ar^1$ preferably denotes phenyl, thienyl, pyridinyl, pyrrolyl, imidazolyl, triazolyl, furanyl, isoxazolyl or oxazolyl, all of which are condensed to a group $Ar^2$.

$Ar^1$-C1: In still another embodiment the group $Ar^1$ preferably denotes phenyl, thienyl, pyridinyl, pyrrolyl, imidazolyl, triazolyl, furanyl, isoxazolyl or oxazolyl, all of which are linked to a group $Ar^2$ via a single bond.

The group $Ar^2$ preferably denotes phenyl, pyridyl, pyrrolyl, dihydropyrrolyl, furanyl, dihydrofuranyl or dioxolyl.

$Ar^1$-B2: In the embodiment $Ar^1$-B2 the group $Ar^1$ even more preferably denotes benzooxazole, benzoimidazole, benzotriazole, benzofuran, 2,3-dihydrobenzofuran, benzo[1,3]dioxole, naphthyl, quinoline or isoquinoline.

$Ar^1$-B3: In this embodiment the group $Ar^1$ most preferably denotes

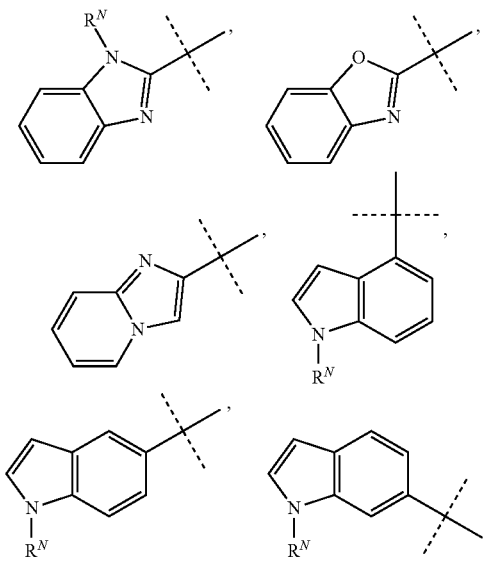

$Ar^1$-C2: In the embodiment $Ar^1$-C1 the group $Ar^1$ even more preferably denotes biphenyl, phenylpyridinyl or pyridinylphenyl; for example 5-phenyl-pyridin-2-yl.

In the hereinbefore mentioned embodiments the group $Ar^1$, including any group $Ar^2$, one or more C-atoms may be substituted independently of one another with a substituent L1; and one or more imino-groups may be substituted independently of one another with a substituent $R^{N0}$.

L0:

The substituent L0 is preferably independently of each other selected from the group consisting of F, Cl, Br, cyano, OH, $C_{1-3}$-alkyl, $C_{2-4}$-alkenyl, $C_{1-3}$-alkyloxy, $C_{1-4}$-alkylcarbonyl, amino, $C_{1-3}$-alkylamino, and di-($C_{1-3}$-alkyl)amino, wherein alkyl-groups may be mono- or polyfluorinated.

Preferred examples of the substituent L0 are F, Cl, Br, cyano, OH, methyl, difluoromethyl, trifluoromethyl, ethyl, propyl, i-propyl, ethenyl, propenyl, methoxy, difluoromethoxy, trifluoromethoxy, ethoxy, propoxy, i-propoxy, methylcarbonyl, ethylcarbonyl, amino, methylamino, and dimethylamino.

L1:

The substituent L1 is preferably independently of each other selected from the group consisting of F, Cl, Br, cyano, OH, $C_{1-3}$-alkyl, $C_{2-4}$-alkenyl, $C_{1-3}$-alkyloxy, $C_{1-4}$-alkylcarbonyl, amino, $C_{1-3}$-alkylamino, di-($C_{1-3}$-alkyl)amino, aminocarbonyl, $C_{1-3}$-alkylaminocarbonyl, di-($C_{1-3}$-alkyl)aminocarbonyl, $C_{1-3}$-alkyl-carbonylamino, and $C_{1-3}$-alkyl-sulfonylamino, wherein alkyl-groups may be mono- or polyfluorinated.

Preferred examples of the substituent L1 are F, Cl, Br, cyano, OH, methyl, difluoromethyl, trifluoromethyl, ethyl, propyl, i-propyl, ethenyl, propenyl, methoxy, difluoromethoxy, trifluoromethoxy, ethoxy, propoxy, i-propoxy, methylcarbonyl, ethylcarbonyl, amino, methylamino, dimethylamino, aminocarbonyl, methylaminocarbonyl, dimethylaminocarbonyl, methylcarbonylamino, and methylsulfonylamino.

n:

The integer n preferably denotes 0, 1, 2 or 3, even more preferably 0, 1 or 2.

W:

W-A: In one embodiment the group W denotes a single bond.

W-B: In another embodiment the group W denotes —C≡C—.

W-C: In still another embodiment the group W denotes —CH═CH—.

W-D: In still another embodiment the group W denotes —CH$_2$—CH$_2$—.

W-E: In still another embodiment the group W denotes —CH$_2$—O—.

$R^1$:

The substituent $R^1$ preferably denotes methyl or ethyl, in particular methyl.

$R^2$:

The substituent $R^2$ preferably denotes H or methyl, in particular H.

$R^3$:

$R^3$-A: The substituent $R^3$ preferably denotes $C_{1-6}$-alkyl, $C_{3-4}$-alkenyl, $C_{3-4}$-alkynyl or $C_{3-6}$-cycloalkyl or $R^{N1}R^{N2}N$—, wherein each of said alkyl, alkenyl, alkynyl and cycloalkyl groups may be substituted with one or more substituents selected from the group consisting of $R^{N1}R^{N2}N$—, $C_{1-4}$-alkyl-O—C(═O)—$R^{N0}N$—, HO—, $C_{1-4}$-alkyloxy, $C_{3-7}$-cycloalkyl, phenyl and pyridinyl, wherein said cycloalkyl, phenyl and pyridinyl may be substituted with one or more substituents L2.

$R^3$-B: The substituent $R^3$ preferably denotes $C_{1-6}$-alkyl, $C_{3-6}$-cycloalkyl, $C_{1-4}$-alkyloxy-$C_{1-3}$-alkyl, $R^{N1}R^{N2}N-$, $R^{N1}R^{N2}N-C_{1-6}$-alkyl, wherein alkyl groups may be mono- or polyfluorinated.

$R^3$-C: Examples of preferred substituents $R^3$ are methyl, difluoromethyl, trifluoromethyl, ethyl, 1-methylethyl, propyl, cyclopropyl, methylamino, ethylamino, dimethylamino, diethylamino, aminopentyl, aminohexyl, dimethylaminopentyl, dimethylaminohexyl, 4-(dimethylaminomethyl)-cyclohexylmethyl and 3-(N-methylpiperazin-1-yl)-propyl.

L2:

The substituent L2 is preferably independently of each other selected from the group consisting of F, Cl, Br, cyano, OH, $C_{1-3}$-alkyl, $C_{1-3}$-alkyloxy, $C_{1-4}$-alkylcarbonyl, amino, $C_{1-3}$-alkylamino, di-($C_{1-3}$-alkyl)amino, amino-$C_{1-3}$-alkyl, $C_{1-3}$-alkylamino-$C_{1-3}$-alkyl, di-($C_{1-3}$-alkyl)amino-$C_{1-3}$-alkyl, pyrrolidinyl-$C_{1-3}$-alkyl, piperazinyl-$C_{1-3}$-alkyl, N—($C_{1-3}$-alkyl)piperazinyl-$C_{1-3}$-alkyl, wherein each alkyl-group may be mono- or polyfluorinated.

Preferred examples of the substituent L2 are F, Cl, Br, cyano, OH, methyl, difluoromethyl, trifluoromethyl, ethyl, propyl, i-propyl, ethenyl, methoxy, difluoromethoxy, trifluoromethoxy, ethoxy, propoxy, i-propoxy, methylcarbonyl, ethylcarbonyl, amino, methylamino, dimethylamino, aminomethyl, methylaminomethyl, dimethylaminomethyl, piperazinylmethyl, N-methylpiperazinylmethyl.

$R^{N0}$:

The substituent $R^{N0}$ preferably denotes H, methyl or ethyl, in particular H or methyl.

$R^{N1}$, $R^{N2}$:

The substituents $R^{N1}$, $R^{N2}$ independently of each other are preferably selected from H, $C_{1-3}$-alkyl, or $R^{N1}$, $R^{N2}$ are linked to each other to form with the N-atom of the $R^{N1}R^{N2}N-$ group a heterocyclic ring selected from the group consisting of pyrrolidinyl, piperidinyl, morpholinyl, thiomorpholinyl, piperazinyl or 4-($C_{1-4}$-alkyl)-piperazinyl.

Preferred examples of the substituents $R^{N1}$, $R^{N2}$ are H, methyl, ethyl or $R^{N1}$, $R^{N2}$ are linked to each other to form with the N-atom of the $-N^{R1}R^{N2}$ group a heterocyclic ring selected from the group consisting of pyrrolidinyl, piperidinyl, piperazinyl or 4-methyl-piperazinyl.

Examples of preferred subgeneric embodiments according to the present invention are set forth in the following table, wherein each substituent group of each embodiment is defined according to the definitions set forth hereinbefore and wherein all other substituents of the formula I or I-RS are defined according to the definitions set forth hereinbefore:

| Embodiment | Formula | W | $Ar^1$ | $R^3$ |
|---|---|---|---|---|
| E-1 | I | W-A | $Ar^1$-A1 | $R^3$-B |
| E-2 | I | W-A | $Ar^1$-A1 | $R^3$-C |
| E-3 | I | W-A | $Ar^1$-A2 | $R^3$-A |
| E-4 | I | W-A | $Ar^1$-A2 | $R^3$-B |
| E-5 | I | W-A | $Ar^1$-A2 | $R^3$-C |
| E-6 | I | W-A | $Ar^1$-B1 | $R^3$-A |
| E-7 | I | W-A | $Ar^1$-B1 | $R^3$-B |
| E-8 | I | W-A | $Ar^1$-B1 | $R^3$-C |
| E-9 | I | W-A | $Ar^1$-B2 | $R^3$-A |
| E-10 | I | W-A | $Ar^1$-B2 | $R^3$-B |
| E-11 | I | W-A | $Ar^1$-B2 | $R^3$-C |
| E-12 | I | W-A | $Ar^1$-B3 | $R^3$-A |
| E-13 | I | W-A | $Ar^1$-B3 | $R^3$-B |
| E-14 | I | W-A | $Ar^1$-B3 | $R^3$-C |
| E-15 | I | W-A | $Ar^1$-A1 | $R^3$-A |
| E-16 | I-RS | W-A | $Ar^1$-A1 | $R^3$-B |
| E-17 | I-RS | W-A | $Ar^1$-A1 | $R^3$-C |
| E-18 | I-RS | W-A | $Ar^1$-A2 | $R^3$-A |
| E-19 | I-RS | W-A | $Ar^1$-A2 | $R^3$-B |
| E-20 | I-RS | W-A | $Ar^1$-A2 | $R^3$-C |
| E-21 | I-RS | W-A | $Ar^1$-B1 | $R^3$-A |
| E-22 | I-RS | W-A | $Ar^1$-B1 | $R^3$-B |
| E-23 | I-RS | W-A | $Ar^1$-B1 | $R^3$-C |
| E-24 | I-RS | W-A | $Ar^1$-B2 | $R^3$-A |
| E-25 | I-RS | W-A | $Ar^1$-B2 | $R^3$-B |
| E-26 | I-RS | W-A | $Ar^1$-B2 | $R^3$-C |
| E-27 | I-RS | W-A | $Ar^1$-B3 | $R^3$-A |
| E-28 | I-RS | W-A | $Ar^1$-B3 | $R^3$-B |
| E-29 | I-RS | W-A | $Ar^1$-B3 | $R^3$-C |
| E-30 | I-RS | W-A | $Ar^1$-A1 | $R^3$-A |

The following compounds, including their tautomers, stereoisomers, mixtures thereof and the salts thereof, are particularly preferred:

(1R,3S)-3-Propionylamino-cyclopentanecarboxylic acid N-biphenyl-4-yl-N-methyl-amide, (1R,3S)-3-Acetylamino-cyclopentanecarboxylic acid N-(4-benzooxazol-2-yl-phenyl)-N-methyl-amide, (1R,3S)-3-Propionylamino-cyclopentanecarboxylic acid N-(4-benzooxazol-2-yl-phenyl)-N-methyl-amide.

Terms and Definitions

Some terms used above and hereinafter to describe the compounds according to the invention will now be defined more closely.

The terms "compound(s) according to this invention", "compound(s) of formula (I)", "compound(s) of the invention" and the like denote the compounds of the formula (I) according to the present invention including their tautomers, stereoisomers, mixtures thereof and the salts thereof, in particular the physiologically acceptable salts thereof, and the solvates of such compounds, including the solvates of such tautomers, stereoisomers and salts thereof.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating", "preventing" and "prophylaxis" are used interchangeably and comprise a treatment of patients at risk to develop a condition mentioned hereinbefore, thus reducing said risk.

When this invention refers to patients requiring treatment or prevention, it relates primarily to treatment and prevention in humans, but the pharmaceutical composition may also be used accordingly in veterinary medicine in mammals.

The term "substituted" as used herein, means that any one or more hydrogens on the designated atom is replaced with a selection from the indicated group, provided that the designated atom's normal valence is not exceeded, and that the substitution results in a stable compound.

The term halogen denotes an atom selected from the group consisting of F, Cl, Br and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n has a value of 2 to 6, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl etc.

The term $C_{2-n}$-alkynyl, wherein n has a value of 2 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as herein-before defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms wherein n is 3 to 10. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one C=C double bond.

The term $C_{3-n}$-cycloheteroalkyl denotes a saturated mono-, bi-, tri- or spirocarbocyclic group with 3-m to n-m C atoms and wherein n denotes 3 to 10 and m denotes 1 to 3 heteroatoms independently selected from $NR^N$, O, S, SO, and $SO_2$, which in addition may have a carbonyl group. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl. Preferably the term $C_{3-6}$-cycloheteroalkyl denotes saturated monocyclic groups with one or two heteroatoms.

The term $C_{3-n}$-cycloalkylcarbonyl denotes a $C_{3-n}$-cycloalkyl-C(=O) group wherein $C_{3-n}$-cycloalkyl is as hereinbefore defined.

The term di-($C_{1-3}$-alkyl)amino comprises amino groups which have identical or two different alkyl groups.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

Compounds of the general formula I can be prepared (partly depending on the nature of the linker group W) by the following methods:

1. Condensation of an acid A-1 with an anilinic compound A-2 with an appropriate coupling reagent such as 1-chloro-N,N,2-trimethyl-propenylamine in a solvent like THF or a solvent mixture, preferably at RT (room temperature).

2. Acylation of an aminocyclopentane derivative A-3 with an appropriate acid chloride containing the $R^3$ moiety and a base like TEA or with an appropriate isocyanate in a solvent like DMF, preferably at RT.

3. Suzuki-type reactions of a iodo compound A-4 with an aryl boronic acid or boronic ester containing the $Ar^1$ moiety (W equals a single bond), using an appropriate palladium catalyst system (e.g. generated in situ from palladium(II) acetate and 2-(di-tert-butylphosphino)biphenyl) and a base like aqueous potassium carbonate in a solvent mixture like methanol, dioxane, DCM, preferably at RT.

4. Sonogashira type reactions of a iodo compound A-4 with an aryl acetylene containing the $Ar^1$ moiety (W equals the alkyne spacer), using an appropriate catalyst system (e.g. [1,1'-Bis(diphenylphosphino)ferrocene]dichloropalladium(II) and copper(I) iodide) and a base like TEA in a solvent like DMF, preferably at RT.

5. Sonogahira type reactions of an alkyne derivative A-5 with an aryl iodide containing the $Ar^1$ moiety under similar conditions as mentioned above.

6. Cycloadditions of an alkyne A-5 with an aryl azide using copper(II) sulphate with the addition of ascorbic acid in a solvent or a solvent mixture like DMF, water, preferably at RT.

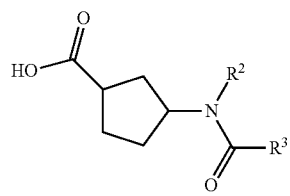

A-1

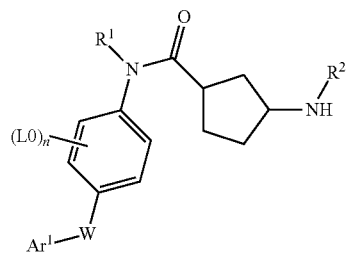

A-3

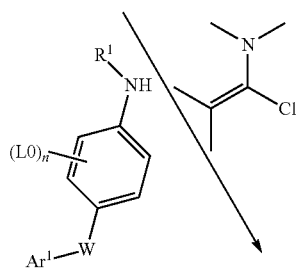

A-2

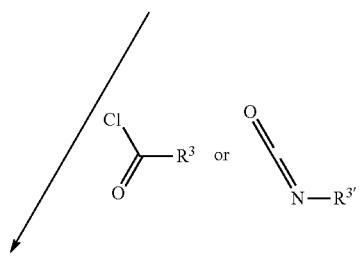

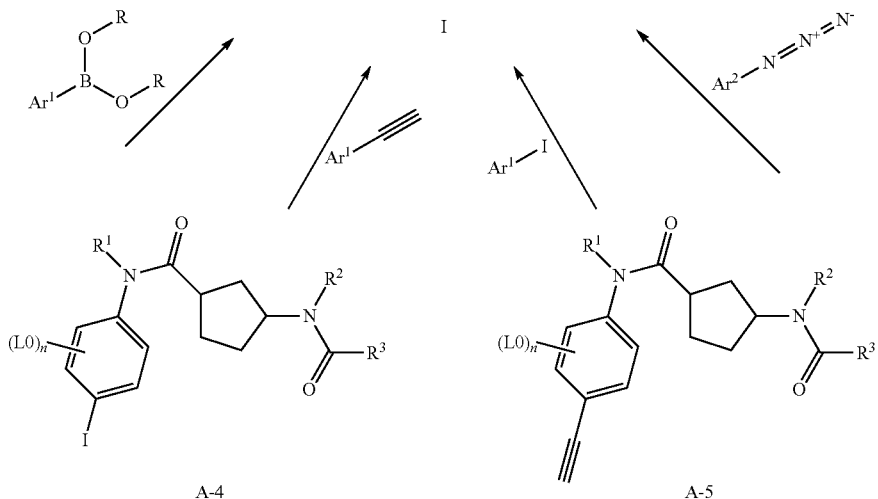

A-4  I  A-5

Acids A-1 can be prepared from the respective 3-(R²—N) cyclopentane carboxylic acids and the acid chloride containing the desired R³ moiety using a base like aqueous sodium hydroxide in a solvent like THF, preferably at RT. 3-Alkylaminocyclopentane carboxylic acids can be prepared from the respective 3-tert-butoxycarbonylaminocyclopentane carboxylic acid by alkylation of the amide nitrogen with the appropriate alkyl iodide using a base like sodium hydride in a solvent like THF (compare R. Brea, et al. Angewandte Chemie, Int. Ed. 44, 35 (2005) 5710-5713) followed by removal of the tert-butoxycarbonyl group, e.g. by stirring the intermediate in TFAA/DCM.

Anilinic compounds A-2 with $R^1$=H can be prepared by reduction of the respective nitro compounds (e.g. under hydrogen pressure with a catalyst like raney nickel). Anilinic compounds A-2 with $R^1$=alkyl can be prepared from the respective desalkyl compounds through a reaction sequence comprising (i) trifluoroacetylation (Trifluoroacetic anhydride, TEA, DCM), (ii) alkylation of the resulting trifluoroacetamide (with the respective alkyl iodide and potassium carbonate in acetone), (iii) removal of the trifluoroacetyl group (with potassium carbonate in methanol/water).

N-[4-(Imidazo[1,2-a]pyridine-2-yl)-phenyl]-N-alkyl-amines can be prepared from the respective 2-(4-nitrophenyl)-imidazo[1,2-a]pyridines as outlined above. The latter can be prepared by reaction of a 2-bromo-1-(4-nitrophenyl)-ethanone with an appropriate 2-aminopyridine in refluxing acetonitrile.

N—($R^1$)—N-[4-(1-$L^1$-1H-benzoimidazol-2-yl)-phenyl]-amines and N—($R^1$)—N-[4-(benzooxazol-2-yl)-phenyl]-amines can be prepared by reacting the respective 2-($L^1$-amino)-anilin or 2-aminophenol, respectively with the appropriate 4-($R^1$-amino)-benzoic acid in polyphosphoric acid at 200-210° C.

Aminocyclopentane derivatives A-3 can be prepared from the respective carbamate derivatives bearing e.g. a BOC— or an Fmoc protecting group on the nitrogen next to $R^2$ by standard deprotection procedures. The carbamate derivatives can be prepared as described above for the condensation of an acid A-1 with an anilinic compound A-2.

Iodo compounds A-4 can be prepared from the respective 4-iodoanilins and acids A-1 as described above.

Alkynes A-5 can be prepared from the respective iodo compounds A-4 by sonogashira type reactions with TMS-acetylene (catalyst system: bis-(triphenylphospine)-palladium dichloride/CuI; base: diisopropylamine; solvent THF; at 0° C.), followed by removal of the TMS group in methanol/aqueous NaOH.

Compounds of the general formula I bearing functional groups in $R^3$, L0, L1, and/or L2 like alcohols, phenolic OH groups, primary or secondary amines can be prepared from precursor compounds bearing well known protective groups attached to one or more of the functional groups in question by standard deprotection methods which are known to the one skilled in the art.

The compounds of general formula I may be resolved into their enantiomers and/or diastereomers, as mentioned before. Thus, for example, cis/trans mixtures may be resolved into their cis and trans isomers, and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography; if the compounds obtained thereafter are racemates, they may be resolved into the enantiomers as mentioned above.

The racemates are preferably resolved by column chromatography on chiral phases or by crystallisation from an optically active solvent or by reacting with an optically active substance which forms salts or derivatives, such as e.g. esters or amides, with the racemic compound. Salts may be formed with enantiopure acids for basic compounds and with enantiopure bases for acidic compounds. Diastereomeric derivatives are formed with enantiopure auxiliary compounds such as e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, di-o-tolyltartaric acid, malic acid, mandelic acid, camphorsulfonic acid, glutamic acid, aspartic acid, or quinic acid. Optically active alcohols applicable as auxiliary may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the physiologically acceptable salts with inorganic or organic acids provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue like, for example, a carboxy group, they may be converted into the salts thereof with inorganic or organic bases, particularly for pharmaceutical use into the physiologically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanol-amine, triethanolamine, N-methyl-D-glucamine, L-lysine, L-arginine, and piperazine.

The compounds according to the invention are advantageously also obtainable using the methods described in the examples that follow, which may also be combined for this purpose with methods known to the skilled man from the literature.

As already mentioned, the compounds of general formula (I) according to the invention, and the salts, in particular the physiologically acceptable salts thereof have valuable pharmacological properties, particularly an inhibitory effect on the enzyme Fatty Acid Synthase (FAS).

Pharmacological Activity

The activity of the compounds of the invention is demonstrated using the following assays:

Human FAS Enzyme Assay.

Fatty acid synthase is an enzyme complex that harbours seven enzymatic activities catalysing the reductive synthesis of long chain fatty acids from acetyl CoA and malonyl CoA to palmitate. When acetyl CoA and malonyl CoA are forming palmitate NADPH is consumed forming NADP. Since NADPH is fluorescent but not NADP the reaction can be measured by analysing the decrease in fluorescence.

Materials:

Acetyl coenzyme A (cat.-no. A-2181) and malonyl coenzyme A (cat.-no. M-4263) are purchased from Sigma. NADPH (cat.-no. 30316) is purchased from Serva. The FAS enzyme is prepared from HeLa cells. All other material is of highest grade commercially available.

Method:

In the plates, 10 µl test compound in distilled water/DMSO (final concentration 0.1% DMSO) are mixed with 35 µl of a mixture of NADPH and acetyl CoA in phosphate buffer (f.c. 326 µM and 60 µM, respectively), and 45 µl FAS enzyme diluted in enzyme buffer. The plates are incubated for 60 minutes at 37° C. The reaction is then started by the addition of 10 µl malonyl CoA dissolved in water (200 µM). The decrease of the optical density in the wells is determined at 37° C. at a wavelength of 340 nm over 10 minutes. From these kinetic data, the slope (i.e. Vmax) is calculated and used for the calculation.

Phosphate Buffer:

100 mM $KH_2PO_4$/$K_2HPO_4$, 1 mM EDTA, 1 mM DTT, pH 7.0

Enzyme Buffer:

20 mM $KH_2PO_4$/$K_2HPO_4$, 1 mM EDTA, 1 mM DTT, 5% glycerol, pH 7.4

Each assay 96 well microtiter plate contains wells with vehicle controls instead of compound (1% DMSO in water) as reference for non-inhibited enzyme activity and wells without malonyl CoA as controls for non-specific NADPH degradation. The analysis of the data is performed by the calculation of the OD decrease in the presence of the test compound compared to the OD decrease of the test control wells after subtraction of the non-specific background without the malonyl CoA substrate (slope(sample)-slope(sample w/o malonyl CoA). An inhibitor of the FAS enzyme will give values between Control values (complete reaction without substance) and complete inhibition. Reported values will include: IC50; Top(Control: nmol NADPH oxidized/min/mg); Bottom (MaxInh: nmol NADPH oxidized/min/mg); RATIO (log(IC50 substance/IC50 control inhibitor)).

$^{14}$C-Acetat Incorporation in N-42 Cells 30000 cells (N-42), in 24 well plates are incubated with the compound dissolved in 500 μL Krebs-Ringer-buffer for 60 min at 37° C., then incubated with 5 μL 1:10 14C-Acetate dilution (1 000 000 dpm) for 4 hours at 37° C. incubation, then washed with 500 μl PBS. 500 μL chloroform/methanol mix 1:1 and 175 μL sodium hydroxide solution was given in each well. The upper fraction is taken away and the lower fraction is vaporized. 50 μL chloroform/methanol mix 1:1 is again given in every well. 10 μL each are taken and given to scintillation vials with 4 mL Ultima Gold. Each vial is measured for 1 minute in a β-Counter.

Cerulenin, a literature known FAS inhibitor is used to validate the assay.

The compounds of general formula I according to the invention for example have $IC_{50}$ values below 10000 nM, particularly below 1000 nM, most preferably below 200 nM.

The compounds described below are inhibitors of FAS with $IC_{50}$ values in the following range as determined in the Human FAS Enzyme assay described above:

| Potency range | Example compounds |
|---|---|
| 500 nM < $IC_{50}$ < 3000 nM | 1.1; 1.4; 1.5; 2.2; 2.3; 2.5; 3.4; 3.5; 4.1; 4.2; 5.2 |
| $IC_{50}$ <= 500 nM | 1.2; 1.3; 1.6; 1.7; 1.8; 2.1; 2.4; 3.1; 3.2; 3.3; 5.1 |

Inhibition of FAS in cellular systems as determined in the assay for $^{14}$C-acetate incorporation in N-42 cells described above is exemplified in the following table:

| Example compound | % control $^{14}$C acetate incorporation |
|---|---|
| 1.2 at 10 μM | 64.1 |
| 1.3 at 10 μM | 81.7 |
| 1.6 at 10 μM | 81.0 |
| 2.1 at 10 μM | 80.8 |
| 3.1 at 10 μM | 76.8 |
| 5.1 at 10 μM | 85.7 |
| Cerulenin at 100 μM | 73.3 |

In vivo activity of the FAS inhibitors on sebaceous glands is determined as exemplified with the following experiment:

Female Wistar rats [Crl:Wi(Han); Charles River, Germany] weighing 200-240 g are conventionally housed in Makrolon type cages at a constant temperature of 22±3° C., on a 12 h light/dark cycle. Food and water are provided ad libitum. The animals (n=7 per group) are orally treated once daily with 3, 10 and 30 mg/kg of compound 1.2 in a suspension with 0.5% Natrosol for seven days. All experimental procedures are conducted according to the German Animal Protection Law. Beginning with day 4 of treatment, at the highest dose effects on skin and coat of the animals could be detected. The rats showed a progressive cranial alopecia, which is manifest especially around the eyes and mouth. Additionally the skin of the mouth and eye lid is reddened and swollen. With longer treatment alopecia and cutaneous lesions also developed at the skin of the back. At day seven the animals are euthanized and representative tissue samples of the eye lid, muzzle and back skin are collected into 4% formaldehyde solution for microscopic examination. After trimming, the fixed tissues are processed, embedded in paraffin, sectioned at a thickness of approximately 4 μm and stained with hematoxylin-eosin (H&E). In all dose groups the microscopic examination reveals treatment-related diffuse atrophy of sebaceous glands of the skin, including the Meibomian glands (glandulae tarsales) of the eyelid, which also are (modified) sebaceous glands. This lesion is sometimes accompanied by a slight inflammatory reaction.

In view of their ability to inhibit the enzyme FAS, the compounds of general formula (I) according to the invention and the corresponding salts thereof are theoretically suitable for the treatment and/or preventative treatment of all those conditions or diseases which may be affected by the inhibition of the FAS activity.

The compounds of formula (I) are useful for the treatment and/or prevention of obesity or overweight, (e.g., promotion of weight loss and maintenance of weight loss), prevention of weight gain (e.g., medication-induced or subsequent to cessation of smoking), for modulation of appetite and/or satiety, eating disorders (e.g. binge eating, bulimia and compulsive eating).

The present compounds of formula (I) are useful for treating or preventing metabolic disorders and/or complications associated with metabolic disorders. Such disorders and/or complications include clinical conditions associated with inherent or induced reduced sensitivity to insulin (insulin resistance) and associated metabolic disorders (also known as the metabolic syndrome). Examples of such clinical conditions are general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAl particle levels and high Apo B levels in the presence of small, dense, low density lipoproteins (LDL) particles, phenotype B. The compounds of the present invention are expected to be useful in treating patients with combined or mixed hyperlipidemias or various degrees of hypertriglyceridemias and postprandial dyslipidemia with or without other manifestations of the metabolic syndrome. The compounds of formula I may also be useful in the treatment of metabolic syndrome and Prader-Willi syndrome.

The present compounds of formula (I) are useful for treating or preventing cardiovascular disorders and/or conditions. Treatment with the present compounds is expected to lower the cardiovascular morbidity and mortality associated with atherosclerosis due to their antidyslipidaemic as well as anti-inflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus, such as the micro-angiopathies causing renal disease, retinal damage and peripheral vascular disease of the lower limbs, is expected to be delayed.

In addition the present compounds of formula (I) are useful for treating or preventing inflammatory and/or neurodegenerative disorders and/or conditions. Examples of such disorders or conditions are polycystic ovarian syndrome and states of inflammatory disease including neurodegenerative disorders such as mild cognitive impairment, Alzheimer's disease, Parkinson's disease and multiple sclerosis.

The compounds of the present invention may also be useful for decreasing sebum production in sebaceous glands of the skin following systemic or topical application. Diseases of the sebaceous gland are acne, seborrhea, sebaceoma and sebaceous carcinoma. The pathogenesis of acne involves lipid (over)production by the sebaceous gland and therefore compound of the present invention may be particularly useful in the treatment of acne.

Moreover, compounds of formula (I) may be useful as antimycobacterial agents in the treatment of mycobacterial infections, such as e.g. tuberculosis.

Compounds of the invention may be useful to treat conditions associated with viral infection like e.g. Hepatitis C, AIDS, Polio, Influenza, warts.

Furthermore, compounds of the invention may be used in the treatment of a broad range of cancers, including e.g. those of the breast, prostate, and ovaries.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers, excipients and/or diluents to produce conventional galenic preparations such as plain or coated tablets, capsules, powders, suspensions, suppositories or preparations for topical applications.

The compounds according to the invention may also be used in conjunction with other active substances, i.e. pharmaceutically active ingredients, particularly for the treatment and/or prevention of the diseases and conditions mentioned above. Other active substances which are suitable for such combinations include for example those which potentiate the therapeutic effect of a FAS inhibitor according to the invention with respect to one of the indications mentioned and/or which allow the dosage of a FAS inhibitor according to the invention to be reduced.

The compounds of the invention may be combined with another therapeutic agent that is useful in the treatment of obesity such as other anti-obesity drugs, that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or G-I motility.

The compounds of the invention may further be combined with another therapeutic agent that is useful in the treatment of disorders associated with obesity such as hypertension, hyperlipidemias, dyslipidemias, diabetes, sleep apnea, asthma, heart disorders, atherosclerosis, macro and micro vascular diseases, liver steatosis, cancer, joint disorders, and gallbladder disorders. For example, a compound of the present invention may be used in combination with a another therapeutic agent that lowers blood pressure or that decreases the ratio of LDL:HDL or an agent that causes a decrease in circulating levels of LDL-cholesterol. In patients with diabetes mellitus the compounds of the invention may also be combined with therapeutic agents used to treat complications related to microangiopathies.

The compounds of the invention may be used alongside other therapies for the treatment of obesity and its associated complications the metabolic syndrome and type 2 diabetes, these include biguanide drugs, insulin (including synthetic insulin analogues) and oral antihyperglycemics (these may be divided into prandial glucose regulators and alpha-glucosidase inhibitors).

In another aspect of the invention, the compounds of formula I, may be administered in association with a PPAR modulating agent. PPAR modulating agents include but are not limited to a PPAR alpha and/or gamma agonist. In addition the combination of the invention may be used in conjunction with a sulfonylurea. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin.

In the present application, the term cholesterol-lowering agent also includes chemical modifications of the HMG-CoA reductase inhibitors, such as esters, prodrugs and metabolites, whether active or inactive.

The present invention also includes a compound of the present invention in combination with an inhibitor of the ileal bile acid transport system (IBAT inhibitor). The present invention also includes a compound of the present invention in combination with a bile acid binding resin.

The present invention also includes a compound of the present invention in combination with a bile acid sequestering agent.

The present invention also includes a compound of the present invention in combination with a further drug selected from the group consisting of a CETP (cholesteryl ester transfer protein) inhibitor; a cholesterol absorption antagonist; a MTP (microsomal transfer protein) inhibitor; a nicotinic acid derivative, including slow release and combination products; a phytosterol compound; probucol; an anti-coagulant; an omega-3 fatty acid; another anti-obesity compound; an aldose reductase inhibitor; a glycogen phosphorylase inhibitor; a glycogen synthase kinase inhibitors; a glucokinase activator; a haemostasis modulator; an antithrombotic; an activator of fibrinolysis; an antiplatelet agent; a thrombin antagonist; a factor Xa inhibitor; an antiplatelet agent; a 5HT transporter inhibitor; an antihypertensive compound for example an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, an AT-I blocker, a saluretic, a diuretic or a vasodilator; a melanin concentrating hormone (MCH) modulator; an NPY receptor modulator; for example an NPY agonist or an NPY2 agonist or an NPY5 antagonist; an Mc4r modulator for example an Mc4r agonist; an Mc3r modulator for example an Mc3r agonist; an orexin receptor modulator for example an antagonist; a phosphoinositidedependent protein kinase (PDK) modulator; or modulators of nuclear receptors for example LXR, FXR, RXR, GR, ERR&alpha, β PAR&alpha, &beta, γ δ and RORalpha; a monoamine transmission-modulating agent, for example a selective serotonin reuptake inhibitor (SSRI), a noradrenaline reuptake inhibitor (NARI), a noradrenaline-serotonin reuptake inhibitor (SNRI), a monoamine oxidase inhibitor (MAOI), a tricyclic antidepressive agent (TCA), a noradrenergic and specific serotonergic antidepressant (NaSSA); an antipsychotic agent; a serotonin receptor modulator; a leptin/leptin receptor modulator; a CBI receptor modulator for example an inverse agonist or an antagonist; a GLK receptor modulator; a DPP-IV inhibitor; a cholesterol absorption inhibitor; a GLP-I agonist; an SGLT-2 inhibitor; a DGAT1 inhibitor; a DGAT2 inhibitor; a DGAT2 inhibitor anti-sense oligonucleotide; a ghrelin antibody; a ghrelin antagonist; an 11beta-HSD-I inhibitor; an UCP-1, 2 or 3 activator.

The present invention also includes a compound of the present invention in combination with an antiproliferative agent.

The present invention also includes a compound of the present invention in combination with an antibacterial, antimycobacterial or antiviral agent.

The present invention also includes a compound of the present invention in combination with one or more therapeutic agents which are suitable in the treatment or prevention of acne, seborrhea, sebaceoma or sebaceous carcinoma, as for example 13-cis-retinoic acid and systemic antiandrogens (for use in women only).

Therefore, in another aspect, this invention relates to the use of a compound according to the invention combined with at least one of the active substances described above as a combination partner, for preparing a pharmaceutical composition which is suitable for the treatment or prevention of diseases or conditions which can be affected by inhibiting the enzyme FAS, in particular diseases or conditions as described hereinbefore.

The use of the compound according to the invention in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention and at least one of the active substances described above as combination partners, optionally together with one or more inert carriers and/or diluents.

The compound according to the invention and the additional active substance to be combined therewith may both be present together in one formulation, for example a tablet or capsule, or separately in two identical or different formulations, for example as a so-called kit-of-parts.

According to an additional further aspect of the present invention there is provided a combination treatment comprising the administration of an effective amount of a compound of the formula I, or a physiologically acceptable salt thereof, optionally together with a pharmaceutically acceptable diluent or carrier, with the simultaneous, sequential or separate administration of very low calorie diets (VLCD) or low-calorie diets (LCD).

The Examples that follow are intended to illustrate the present invention without restricting it. The terms "ambient temperature" and "room temperature" are used interchangeably and designate a temperature of about 20° C.

Preliminary Remarks:

As a rule, $^1$H-NMR and/or mass spectra have been obtained for the compounds prepared. The $R_f$ values are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. Silica gel made by Millipore (MATREX™, 35-70 my) is used for chromatographic purification. Alox (E. Merck, Darmstadt, aluminium oxide 90 standardised, 63-200 μm, Item no. 1.01097.9050) is used for chromatographic purification.

The HPLC data given are measured under the following parameters:

mobile phase A: water:formic acid 99.9:0.1
mobile phase B: acetonitrile:formic acid 99.9:0.1

Method 1:

Analytical column: Atlantis C18; 2.5 μm, 4.6 mm×30 mm; column temperature: room temperature. Gradient:

| time in min | % A | % B | flow rate in mL/min |
|---|---|---|---|
| 0.00 | 95.0 | 5.0 | 1.00 |
| 0.10 | 95.0 | 5.0 | 1.00 |
| 3.10 | 2.0 | 98.0 | 1.00 |
| 4.50 | 2.0 | 98.0 | 1.00 |
| 5.00 | 95.0 | 5.0 | 1.00 | mobile phase A: water:trifluoroacetic acid 99.9:0.1
mobile phase B: acetonitrile:trifluoroacetic acid 99.9:0.1

Method 2:

Analytical column: XTerra C18; 3.5 μm, 4.6 mm×50 mm; column temperature: 40° C. Gradient:

| time in min | % A | % B | flow rate in mL/min |
|---|---|---|---|
| 0.0 | 95.0 | 5.0 | 1.50 |
| 2.0 | 2.00 | 98.0 | 1.50 |
| 2.5 | 2.00 | 98.0 | 1.50 |
| 2.9 | 95.0 | 5.0 | 1.50 |

Method 3:

Analytical column: XTerra C18; 3.5 μm, 4.6 mm×50 mm; column temperature: 40° C. Gradient:

| time in min | % A | % B | flow rate in mL/min |
|---|---|---|---|
| 0.0 | 95.0 | 5.0 | 1.50 |
| 2.0 | 2.00 | 98.0 | 1.50 |
| 2.5 | 2.00 | 98.0 | 1.50 |
| 2.9 | 95.0 | 5.0 | 1.50 |

Method 4:

Analytical column: XTerra C18; 3.5 μm, 4.6 mm×50 mm; column temperature: 40° C. Gradient:

| time in min | % A | % B | flow rate in mL/min |
|---|---|---|---|
| 0.0 | 95.0 | 5.0 | 1.50 |
| 2.0 | 0.00 | 100.0 | 1.50 |
| 2.49 | 0.00 | 100.0 | 1.50 |
| 2.5 | 95.0 | 5.0 | 1.50 |

The following abbreviations are used above and hereinafter:

DIPEA Diisopropyl-ethylamine
DMF N,N-dimethylformamide
EII electron impact ionisation
HCl hydrochloric acid
NaH Sodium hydride
RT ambient temperature (about 20° C.)
TBTU 2-(1H-benzotriazol-1-yl)-1,1,3,3-tetramethyluronium-tetrafluoroborate
TEA Triethylamine
THF tetrahydrofuran
DCM methylene chloride
Fmoc 9H-Fluoren-9-yl-methoxycarbonyl
TFAA Trifluoroacetic acid
BOC tert-Butoxycarbonyl
TMS Trimethylsilyl Preparation of the Starting Compounds:

Example I

Example I.1

(1R,3S)-3-Amino-cyclopentanecarboxylic acid-N-[4-(1H-benzoimidazol-2-yl)-phenyl]-N-methyl-amide

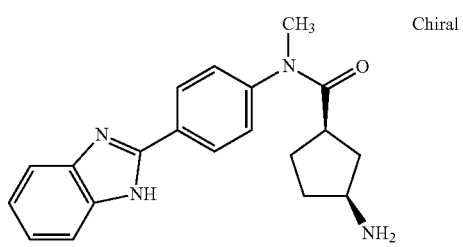 [SMILES: CN(C(=O)[C@@H]1CC[C@H](N)C1)c1ccc(-c2nc3ccccc3[nH]2)cc1]

I.1.a

N-[4-(1H-Benzoimidazol-2-yl)-phenyl]-N-methyl-amine 5.00 g (46.2 mmol) o-Phenylene diamine and 6.99 g (46.2 mmol) 4-(methylamino)benzoic acid are stirred in 40.0 g polyphosphoric acid at 210° C. for 4 hours. The mixture is cooled to 80° C., poured into water and stirred over night at RT. The mixture is alkalinized with sodium hydroxide solution. The precipitate is filtered off and washed with water. The product is dried in vacuo at 70° C.

Yield: 9.87 g (96% of theory)
$C_{14}H_{13}N_3$
EII Mass spectrum: m/z=224 $[M+H]^+$
$R_f$ value: 0.40 (silica gel, DCM/methanol=9:1)

I.1.b (1R,3S)-3-Amino-cyclopentanecarboxylic acid-N-[4-(1H-benzoimidazol-2-yl)-phenyl]-N-methyl-amide 395.0 mg (1.12 mmol) (1S,3R)—(N)-Fmoc-1-aminocyclopentane-3-carboxylic acid is dissolved in 30 mL THF. 270.0 mg (1.14 mmol) Diphenylphosphinic chloride and 650.0 µL (4.63 mmol) TEA are added and stirred for 10 minutes at RT. 250.0 mg (1.12 mmol) [4-(1H-Benzoimidazol-2-yl)-phenyl]-methyl-amine (educt I.1.a) is added and stirred at 60° C. over night. The mixture is filtered through basic alumina, washed with a mixture of DCM/methanol (9:1). The solvent is removed under reduced pressure. The residue is dissolved in THF and 5 mL piperidine is added. The mixture is stirred at RT over night. The substance is purified by silica gel column chromatography (gradient: DCM:methanol/ammonia (9/1); 100:0->5:1). The solvent is evaporated.

Yield: 211.0 mg (56% of theory)
$C_{20}H_{22}N_4O$
EII Mass spectrum: m/z=335 $[M+H]^+$ Example II Example II.1

(1R,3S)-3-Amino-cyclopentanecarboxylic acid N-biphenyl-4-yl-N-methyl-amide

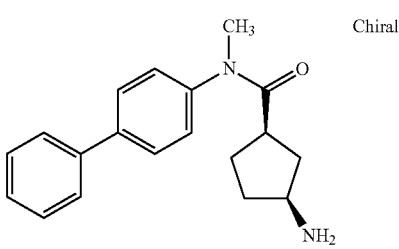 [SMILES: CN(C(=O)[C@@H]1CC[C@H](N)C1)c1ccc(-c2ccccc2)cc1]

II.1.a

N-(Biphenyl-4-yl)-2,2,2-trifluoro-acetamide 5.00 g (24.3 mmol) 4-Aminobiphenyl and 4.20 mL (29.9 mmol) TEA is stirred in 50 mL DCM under cooling with an ice bath. 4.20 mL (30.2 mmol) Trifluoroacetic anhydride is added drop wise. The mixture is allowed to warm to RT and stirred for 1 hour. The mixture is washed with water. The organic phase is dried and the solvent is evaporated.

Yield: 4.30 g (67% of theory)
$C_{14}H_{10}F_3NO$
EII Mass spectrum: m/z=264 $[M-H]^-$
$R_f$ value: 0.66 (silica gel, DCM)

II.1.b

N-(Biphenyl-4-yl)-N-methyl-2,2,2-trifluoro-acetamide 13.00 g (49.0 mmol) N-(Biphenyl-4-yl)-2,2,2-trifluoro-acetamide (II.1.a) is dissolved in 200 mL acetone and 13.5 g (98.0 mmol) potassium carbonate is added. 3.50 mL (55.7 mmol) methyl iodide is added and the mixture is stirred at RT over night. The solvent is evaporated. The residue is taken up in water and extracted with ethyl acetate. The organic phase is dried and the solvent is evaporated.

Yield: 11.53 g (84% of theory)
$C_{15}H_{12}F_3NO$
EII Mass spectrum: m/z=280 [M+H]$^+$
$R_f$ value: 0.90 (silica gel, DCM)

II.1.c

Biphenyl-4-yl-methyl-amine hydrochloride 11.5 g (0.04 mol) N-(Biphenyl-4-yl)-N-methyl-2,2,2-trifluoro-acetamide (II.1.b) and 5.57 g (0.04 mol) potassium carbonate are stirred in 120 mL methanol/water over night. The mixture is extracted with ethyl acetate. The organic phase is dried and evaporated. Ethyl acetate/HCl is added. The precipitate is filtered off and dried.

Yield: 8.60 g (95% of theory)
$C_{13}H_{13}N*HCl$
EII Mass spectrum: m/z=184 [M+H]$^+$
$R_f$ value: 0.80 (silica gel, DCM)

II.1.d

(1R,3S)-3-Amino-cyclopentanecarboxylic acid N-biphenyl-4-yl-N-methyl-amide 351.4 mg (1.00 mmol) (1S,3R)—(N)-Fmoc-1-aminocyclopentane-3-carboxylic acid is stirred in DMF at RT. 500.0 mg (4.00 mmol) DIPEA and 417.3 mg (1.3 mmol) TBTU are added. 219.0 mg (1.0 mmol) Biphenyl-4-yl-methyl-amine hydrochloride (II.1.c) is added and the mixture is stirred at RT over night. The solvent is evaporated. The product is purified by RP-HPLC (water+5-95% acetonitrile (with addition of 0.1% TFA)) and lyophilized. The residue is taken up in DCM and diethylamine is added. After 2 hours of stirring at RT the mixture is filtered and evaporated.

Yield: 150.0 mg (51% of theory)
$C_{19}H_{22}N_2O$
EII Mass spectrum: m/z=517 [M+H]$^+$

Example III

Example III.1

(1R,3S)-3-Amino-cyclopentanecarboxylic acid-N-methyl-N-[4-(1-methyl-1H-benzoimidazol-2-yl)-phenyl]-amide

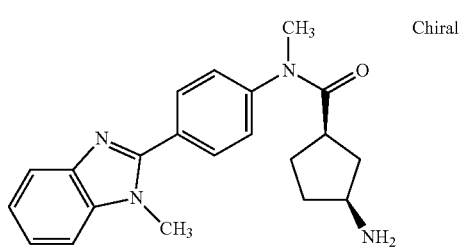 [SMILES: CN(C(=O)[C@@H]1CC[C@H](N)C1)c1ccc(-c2nc3ccccc3n2C)cc1]

III.1.a

N-Methyl-N-[4-(1-methyl-1H-benzoimidazol-2-yl)-phenyl]-amine 10.14 mL (86.5 mmol) N-Methyl-o-phenylenediamine and 13.08 g (86.5 mmol) 4-(methylamino)benzoic acid are stirred in 70.0 g polyphosphoric acid at 200° C. for 3 hours. The mixture is cooled to 80° C., poured into water and stirred over night at RT. The mixture is alkalinized with sodium hydroxide solution. The precipitate is filtered off and washed with water. The product is dried in vacuo at 50° C.

Yield: 18.54 g (90% of theory)
$C_{15}H_{15}N_3$
EII Mass spectrum: m/z=238 [M+H]$^+$

III.1.b

(1R,3S)-3-Amino-cyclopentanecarboxylic acid-N-methyl-N-[4-(1-methyl-1H-benzoimidazol-2-yl)-phenyl]-amide The compound is synthesised analogously to the method described above (example I.1.b) with N-Methyl-N-[4-(1-methyl-1H-benzoimidazol-2-yl)-phenyl]-amine (educt III.1.a) and (1S,3R)—(N)-Fmoc-1-aminocyclopentane-3-carboxylic acid as educts.

Yield: 33% of theory
$C_{21}H_{24}N_4O$
EII Mass spectrum: m/z=349 [M+H]$^+$

Example IV

Example IV.1

(1R,3S)-3-Propionylamino-cyclopentanecarboxylic acid

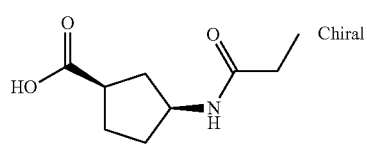

100.0 mg (0.77 mmol) (1R,3S)-3-Aminocyclopentane carboxylic acid is stirred in 2.0 mL THF and 0.77 mL (1.55 mmol) sodium hydroxide solution (2 mol/l). 74.0 μL (0.85 mmol) Propionyl chloride is added drop wise and the mixture is stirred at RT over night. The solvent is evaporated. The mixture is stirred at RT over night. The product is purified by RP-HPLC (water+5-95% acetonitrile (with addition of 0.1% TFA)) and lyophilized.

Yield: 80.0 mg (56% of theory)
$C_9H_{15}NO_3$
EII Mass spectrum: m/z=184 [M−H]$^−$

Example IV.2

N-[4-(Imidazo[1,2-a]pyridin-2-yl)-phenyl]-N-methyl-amine trifluoro acetate

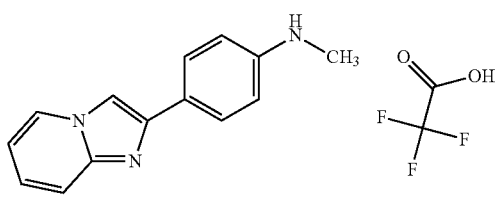 [SMILES: CNc1ccc(-c2cn3ccccc3n2)cc1 ; O=C(O)C(F)(F)F]

Example IV.2.a 2-(4-Nitro-phenyl)-imidazo[1,2-a]pyridine 5.00 g (20.49 mmol) 2-Bromo-1-(4-nitrophenyl)-ethanone and 3.86 g (40.98 mmol) 2-aminopyridine are heated to reflux in 50 mL acetonitrile for 3 hours. The mixture is allowed to cool to RT. The solvent is evaporated. The residue is suspended in ethanol and alkalinized with ammonia solution. The precipitate is filtered off, washed with diethyl ether and dried.
Yield: 4.50 g (92% of theory)
$C_{13}H_9N_3O_2$
EII Mass spectrum: m/z=240 [M+H]$^+$

Example IV.2.b 4-(Imidazo[1,2-a]pyridin-2-yl)-phenylamine 4.50 g (18.8 mmol) 2-(4-Nitro-phenyl)-imidazo[1,2-a]pyridine and 0.45 g Raney-Nickel are stirred at RT under hydrogen (50 psi) in 50 mL ethanol and 50 mL ethyl acetate. The mixture is filtered and the solvent is evaporated.
Yield: 3.32 g (84% of theory)
$C_{13}H_{11}N_3$
EII Mass spectrum: m/z=210 [M+H]$^+$

Example IV.2.c

N-[4-(Imidazo[1,2-a]pyridin-2-yl)-phenyl]-2,2,2-trifluoro-acetamide

The compound is synthesised analogously to the method described above (educt II.1.a) with 4-(Imidazo[1,2-a]pyridin-2-yl)phenylamine (educt IV.2.b) as educt.
Yield: 93% of theory
$C_{15}H_{10}F_3N_3O$
EII Mass spectrum: m/z=306 [M+H]$^+$
$R_f$ value: 0.50 (silica gel, DCM/methanol: 9/1)

Example IV.2.d

N-[4-(Imidazo[1,2-a]pyridin-2-yl)-phenyl]-N-methyl-2,2,2-trifluoro-acetamide 0.95 g (3.11 mmol) N-[4-(Imidazo[1,2-a]pyridin-2-yl)-phenyl]-2,2,2-trifluoro-acetamide (educt IV.2.c) is dissolved in 10 mL DMF. 0.14 g (3.73 mmol) NaH (60% in mineral oil) is added. Then 195 μL (3.11 mmol) methyl iodide is added and the mixture is stirred at RT over night. The mixture is poured into water. The precipitate is filtered off and dried in vacuo at 50° C.
Yield: 0.75 g (76% of theory)
$C_{16}H_{12}F_3N_3O$
EII Mass spectrum: m/z=320 [M+H]$^+$

Example IV.2.e

N-(4-[Imidazo[1,2-a]pyridin-2-yl)-phenyl]-N-methyl-amine trifluoro acetate 0.75 g (2.35 mmol) 2,2,2-Trifluoro-N-(4-imidazo[1,2-a]pyridin-2-yl-phenyl)-N-methyl-acetamide (educt IV.2.d) and 0.65 g (4.70 mmol) potassium carbonate are suspended in 20 mL methanol and 20 mL water and stirred at 50° C. over night. The mixture is extracted with ethyl acetate. The organic phase is dried and evaporated.
The product is purified by RP-HPLC (water+5-95% acetonitrile (with addition of 0.1% TFA)) and lyophilized.
Yield: 0.45 g (57% of theory)
$C_{14}H_{13}N_3 * C_2HF_3O_2$
EII Mass spectrum: m/z=224 [M+H]$^+$

Example V.1

(1R,3S)-3-Amino-cyclopenatnecarboxylic acid N-(4-benzooxazol-2-yl-phenyl)-N-methyl-amide trifluoro acetate

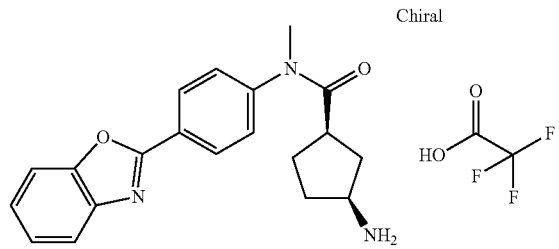 [SMILES: CN(C(=O)[C@@H]1CC[C@H](N)C1)c1ccc(-c2nc3ccccc3o2)cc1 ; O=C(O)C(F)(F)F]

Example V.1.a (4-Benzooxazol-2-yl-phenyl)-methyl-amine 15.1 g (138.0 mmol) 2-Aminophenol and 21.5 g (138.0 mmol) 4-Methyl-aminobenzoic acid are heated up to 205° C. in 150 mL polyphosphoric acid for 4 hours. The mixture is cooled to 80° C., poured into water and stirred overnight at RT. The mixture is alkalinized with sodium hydroxide solution. The precipitate is filtered off and washed with water. The product is dried.
Yield: 25.6 g (83% of theory)
$C_{14}H_{12}N_2O$
EII Mass spectrum: m/z=225 [M+H]$^+$

Example V.1.b

{3-[N-(4-Benzooxazol-2-yl-phenyl)-N-methyl-carbamoyl]-cyclopentyl}-carbamic acid 9H-fluoren-9-yl-methyl-ester 250 mg (0.71 mmol) (−)-(1S,3R)—N-Fmoc-1-Aminocyclopentane-3-carboxylic acid and 0.14 mL (1.07 mmol)

1-chloro-N,N,2-trimethylpropenyldiamine are dissolved in 5 mL DCM and stirred for 2 hours. The resulting product is added to a mixture of 159.6 mg (0.71 mmol) (4-Benzooxazol-2-yl-phenyl)-methyl-amine and 0.14 mL (1.07 mmol) 2,4,6-collidine in 5 mL DCM. The reaction mixture is stirred overnight at RT. The mixture is concentrated under reduced pressure. The residue is taken up in water and extracted with DCM. The organic layer is dried, filtered off and concentrated under reduced pressure. The product is purified by RP-HPLC (water+5-95% acetonitrile (with addition of 0.1% TFA)). The solvent is evaporated.

Yield: 327 mg (82% of theory)
$C_{35}H_{31}N_3O_4$
EII Mass spectrum: m/z=558 [M+H]$^+$ Example V.1.c (1R,3S)-3-Amino-cyclopenatnecarboxylic acid N-(4-benzooxazol-2-yl-phenyl)-N-methyl-amide trifluoro acetate 238 mg (0.43 mmol) {3-[(4-Benzooxazol-2-yl-phenyl)-methyl-carbamoyl]-cyclopentyl}-carbamic acid 9H-fluoren-9-yl-methyl-ester and 0.35 mL (3.31 mmol) diethylamine are stirred overnight at RT in 10 mL THF. Further diethylamine is added and the mixture is stirred for another day and than for 2 hours at 40° C. The residue is concentrated under reduced pressure. The product is purified by RP-HPLC (water+5-95% acetonitrile (with addition of 0.1% TFA)). The solvent is evaporated.

Yield: 220 mg (84% of theory)
$C_{20}H_{21}N_3O_2 * C_2HF_3O_2$
EII Mass spectrum: m/z=336 [M+H]$^+$ Preparation of the End Compounds:

Example 1.1

(1R,3S)-3-(3-Ethyl-ureido)-cyclopentanecarboxylic acid N-(4-benzooxazol-2-yl-phenyl)-N-methyl-amide

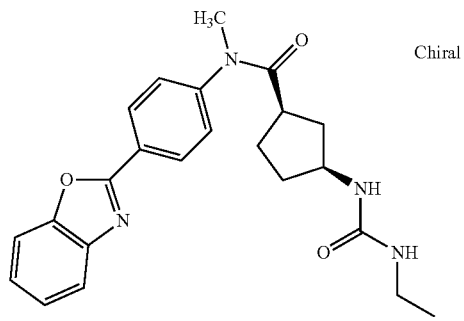 [SMILES: CCNC(=O)N[C@H]1CC[C@@H](C(=O)N(C)c2ccc(-c3nc4ccccc4o3)cc2)C1]

55.9 mg (0.12 mmol) of Example V.1 and 0.01 mL (0.15 mmol) ethyl isocyanate are dissolved in 3 mL DMF and 0.02 mL (0.15 mmol) TEA. The mixture is stirred at RT for 1 hour. The solvent is evaporated and the residue is taken up in DCM and is washed with water. The organic layer is separated, dried and concentrated under reduced pressure.

Yield: 21.0 mg (42% of theory)
$C_{23}H_{26}N_4O_3$
EII Mass spectrum: m/z=407 [M+H]$^+$
ret. time: 2.85 min (HPLC method 1)

Example 1.2

(1R,3S)-3-Propionylamino-cyclopentanecarboxylic acid N-(4-benzooxazol-2-yl-phenyl)-N-methyl-amide

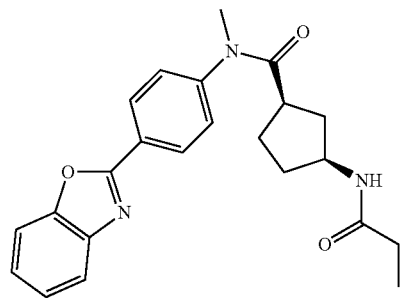

256 mg (0.76 mmol) educt V.1, 0.13 mL (1.53 mmol) propionyl chloride and 0.15 mL (1.53 mmol) TEA are stirred in 5 ml DMF for 2 hours at RT. The mixture is concentrated under reduced pressure. The residue is taken up in water and extracted with DCM. The organic layer is separated, dried and concentrated under reduced pressure.

Yield: 130 mg (44% of theory)
$C_{23}H_{25}N_3O_3$
EII Mass spectrum: m/z=392 [M+H]$^+$
ret. time: 2.96 min (HPLC method 1)

Example 1.3

(1R,3S)-3-Acetylamino-cyclopentanecarboxylic acid N-(4-benzooxazol-2-yl-phenyl)-N-methyl-amide

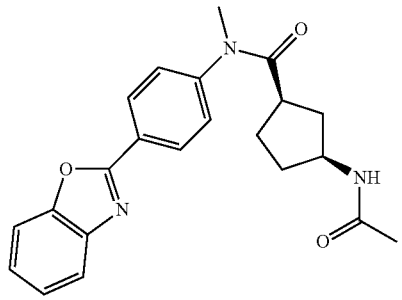

The compound is synthesised analogously to the method described above (example 1.2) with educt V.1 and acetyl chloride as educts.

Yield: 24.0 mg (71% of theory)
$C_{22}H_{23}N_3O_3$
EII Mass spectrum: m/z=378 [M+H]$^+$
ret. time: 2.63 min (HPLC method 1)

Example 1.4

(1R,3S)-3-(6-Dimethylamino-hexanoylamino)-cyclopentanecarboxylic acid N-(4-benzooxazol-2-yl-phenyl)-N-methyl-amide

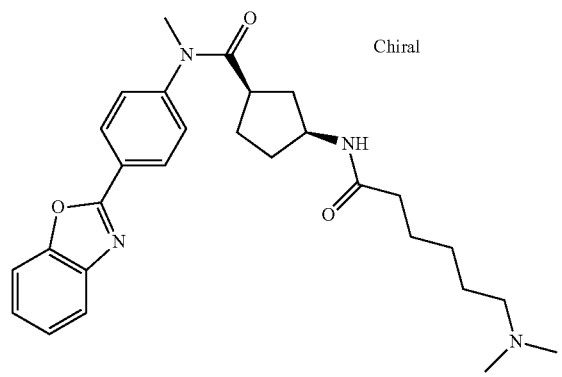 [SMILES: CN(C)CCCCCC(=O)N[C@H]1CC[C@@H](C(=O)N(C)c2ccc(-c3nc4ccccc4o3)cc2)C1 ; "Chiral"]

44.0 mg (0.0.9 mmol) of Example V.1, 25.7 mg (0.11 mmol) 6-dimethylamino hexanoic acid hydrobromide, 0.03 mL (0.27 mmol) TEA and 42.9 mg (0.13 mmol) TBTU are dissolved in 3 mL DMF. The mixture is stirred overnight. The reaction mixture is diluted with water and extracted with DCM. The organic layer is separated, dried and concentrated under reduced pressure. The residue is purified by RP-HPLC (water+5-95% acetonitrile (with addition of 0.1% TFA)).

Yield: 19.0 mg (45% of theory)

$C_{28}H_{36}N_4O_3$

EII Mass spectrum: m/z=477 [M°H]$^+$ ret. time: 2.24 min (HPLC method 1)

Example 1.5

(1R,3S)-3-(2-Methoxy-acetylamino)-cyclopentanecarboxylic acid N-(4-benzooxazol-2-yl-phenyl)-N-methyl-amide

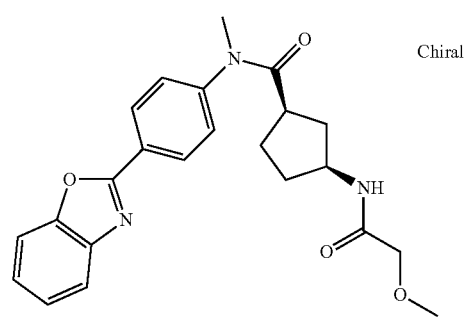 [SMILES: COCC(=O)N[C@H]1CC[C@@H](C(=O)N(C)c2ccc(-c3nc4ccccc4o3)cc2)C1]

The compound is synthesised analogously to the method described above (example 1.2) with educt V.1 and methoxy-acetyl chloride as educts.

Yield: 35.0 mg (68% of theory)

$C_{23}H_{25}N_3O_4$

EII Mass spectrum: m/z=408 [M+H]$^+$ ret. time: 2.86 min (HPLC method 1)

Example 1.6

(1R,3S)-3-Butyrylamino-cyclopentanecarboxylic acid N-(4-benzooxazol-2-yl-phenyl)-N-methyl-amide

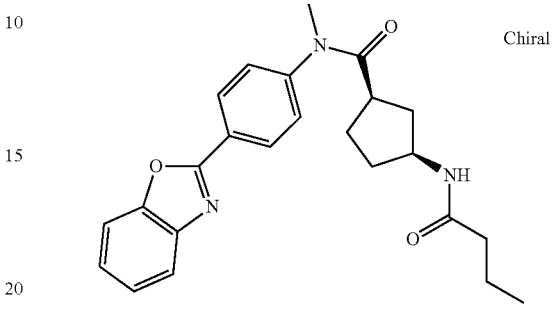

The compound is synthesised analogously to the method described above (example 1.2) with educt V.1 and butyryl chloride as educts.

Yield: 20.0 mg (44% of theory)

$C_{24}H_{27}N_3O_3$

EII Mass spectrum: m/z=406 [M+H]$^+$ ret. time: 3.04 min (HPLC method 1)

Example 1.7

(1R,3S)-3-(3,3-Dimethyl-ureideo)-cyclopentanecarboxylic acid N-(4-benzooxazol-2-yl-phenyl)-N-methyl-amide

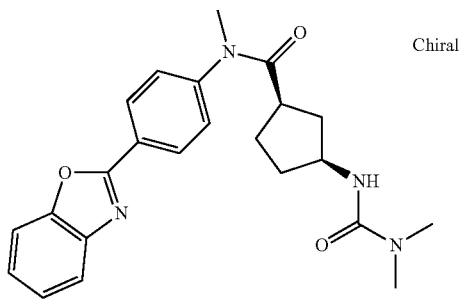 [SMILES: CN(C)C(=O)N[C@H]1CC[C@@H](C(=O)N(C)c2ccc(-c3nc4ccccc4o3)cc2)C1]

The compound is synthesised analogously to the method described above (example 1.2) with educt V.1 and dimethyl-carbamyl chloride as educts.

Yield: 43.0 mg (95% of theory)

$C_{23}H_{26}N_4O_3$

EII Mass spectrum: m/z=407 [M+H]$^+$ ret. time: 2.96 min (HPLC method 1)

Example 1.8

(1R,3S)-3-(2,2-Difluoro-acetylamino)-cyclopentanecarboxylic acid N-(4-benzooxazol-2-yl-phenyl)-N-methyl-amide

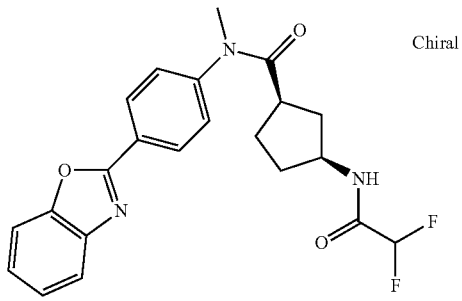 [SMILES: CN(C(=O)[C@@H]1CC[C@H](NC(=O)C(F)F)C1)c1ccc(-c2nc3ccccc3o2)cc1]

The compound is synthesised analogously to the method described above (example 1.4) with educt V.1 and difluoroacetic acid as educts.

Yield: 37.0 mg (72% of theory)
$C_{22}H_{21}F_2N_3O_3$
EII Mass spectrum: m/z=414 [M+H]$^+$
ret. time: 3.11 min (HPLC method 1)

Example 2

Example 2.1

(1R,3S)-3-Propionylamino-cyclopentanecarboxylic acid N-[4'-(1H-benzoimidazol-2-yl)-phenyl]-N-methyl-amide

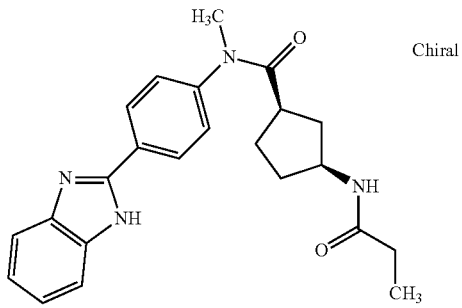 [SMILES: CCC(=O)N[C@H]1CC[C@@H](C(=O)N(C)c2ccc(-c3nc4ccccc4[nH]3)cc2)C1]

The compound is synthesised analogously to the method described above (example 1.2) with educt 1.1 and propionyl chloride as educts.

Yield: 32.0 mg (32% of theory)
$C_{23}H_{26}N_4O_2$
EII Mass spectrum: m/z=391 [M+H]$^+$
ret. time: 1.39 min (HPLC method 1)

Example 2.2

(1R,3S)-3-Acetylamino-cyclopentanecarboxylic acid N-[4'-(1H-benzoimidazol-2-yl)-phenyl]-N-methyl-amide

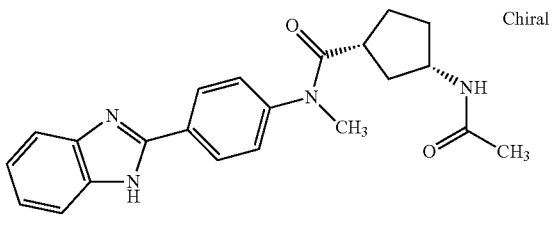 [SMILES: CC(=O)N[C@H]1CC[C@@H](C(=O)N(C)c2ccc(-c3nc4ccccc4[nH]3)cc2)C1]

The compound is synthesised analogously to the method described above (example 1.2) with educt 1.1 and acetyl chloride as educts.

Yield: 10.0 mg (59% of theory)
$C_{22}H_{24}N_4O_2$
EII Mass spectrum: m/z=377 [M+H]$^+$
ret. time: 1.31 min (HPLC method 4)

Example 2.3

(1R,3S)-3-Isobutyrylamino-cyclopentanecarboxylic acid N-[4'-(1H-benzoimidazol-2-yl)-phenyl]-N-methyl-amide

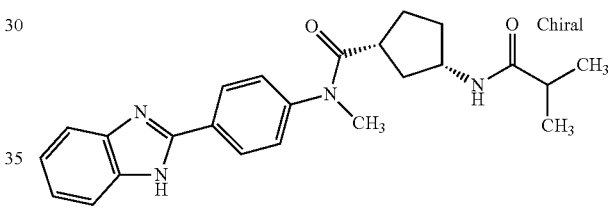

The compound is synthesised analogously to the method described above (example 1.2) with educt I.1 and isobutyryl chloride as educts.

Yield: 10.2 mg (56% of theory)
$C_{24}H_{28}N_4O_2$
EII Mass spectrum: m/z=405 [M+H]$^+$
ret. time: 1.64 min (HPLC method 4)

Example 2.4

(1R,3S)-3-(3-Ethyl-ureido)-cyclopentanecarboxylic acid N-[4'-(1H-benzoimidazol-2-yl)-phenyl]-N-methyl-amide

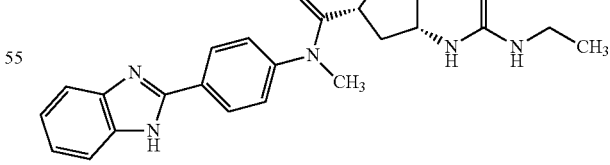

The compound is synthesised analogously to the method described above (example 1.1) with educt 1.1 and ethyl isocyanate as educts.

Yield: 8.3 mg (46% of theory)
$C_{23}H_{27}N_5O_2$
EII Mass spectrum: m/z=406 [M+H]$^+$
ret. time: 1.58 min (HPLC method 4)

Example 2.5

(1R,3S)-3-(6-Dimethylamino-hexanoylamino)-cyclopentanecarboxylic acid N-[4'-(1H-benzoimidazol-2 yl)-phenyl]-N-methyl-amide

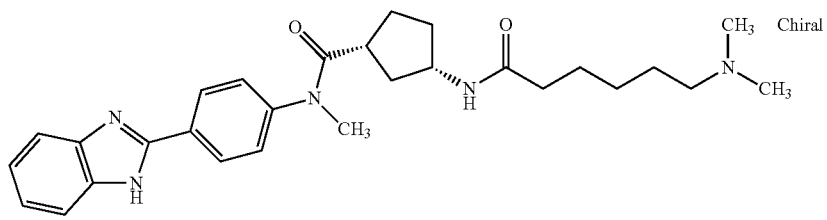 [SMILES: CN(C)CCCCCC(=O)N[C@H]1CC[C@@H](C(=O)N(C)c2ccc(-c3nc4ccccc4[nH]3)cc2)C1]

The compound is synthesised analogously to the method described above (example 1.4) with educt I.1 and 6-dimethylamino-hexanoic acid hydrobromide as educts.
Yield: 14.2 mg (54% of theory)
$C_{28}H_{37}N_5O_2$
EII Mass spectrum: m/z=476 [M+H]$^+$
ret. time: 1.28 min (HPLC method 4)

Example 3

Example 3.1

(1R,3S)-3-Propionylamino-cyclopentanecarboxylic acid N-biphenyl-4-yl-N-methyl-amide

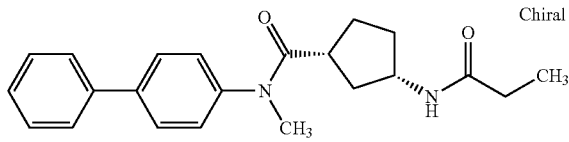 [SMILES: CCC(=O)N[C@H]1CC[C@@H](C(=O)N(C)c2ccc(-c3ccccc3)cc2)C1]

The compound is synthesised analogously to the method described above (example 1.2) with educt II.1 and propionyl chloride as educt.
Yield: 9.1 mg (58% of theory)
$C_{22}H_{26}N_2O_2$
EII Mass spectrum: m/z=351 [M+H]$^+$
ret. time: 2.05 min (HPLC method 4)

Example 3.2

(1R,3S)-3-Isobutyrylamino-cyclopentanecarboxylic acid N-biphenyl-4-yl-N-methyl-amide

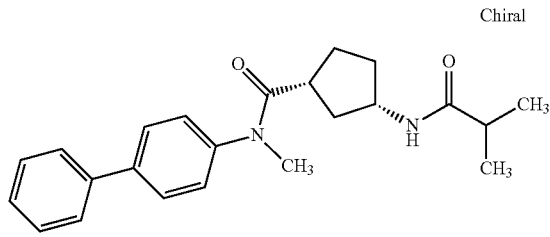 [SMILES: CC(C)C(=O)N[C@H]1CC[C@@H](C(=O)N(C)c2ccc(-c3ccccc3)cc2)C1]

The compound is synthesised analogously to the method described above (example 1.2) with educt II.1 and isobutyryl chloride as educts.
Yield: 10.5 mg (64% of theory)
$C_{23}H_{28}N_2O_2$
EII Mass spectrum: m/z=365 [M+H]$^+$
ret. time: 2.37 min (HPLC method 4)

Example 3.3

(1R,3S)-3-Acetylamino-cyclopentanecarboxylic acid N-biphenyl-4-yl-N-methyl-amide

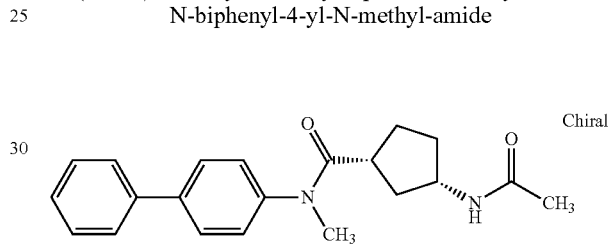

The compound is synthesised analogously to the method described above (example 1.2) with educt 11.1 and acetyl chloride as educts.
Yield: 5.0 mg (3% of theory)
$C_{21}H_{24}N_2O_2$
EII Mass spectrum: m/z=367 [M+H]$^+$
ret. time: 2.77 min (HPLC method 1)

Example 3.4

(1R,3S)-3-(3-Ethyl-ureido)-cyclopentanecarboxylic acid N-biphenyl-4-yl-N-methyl-amide

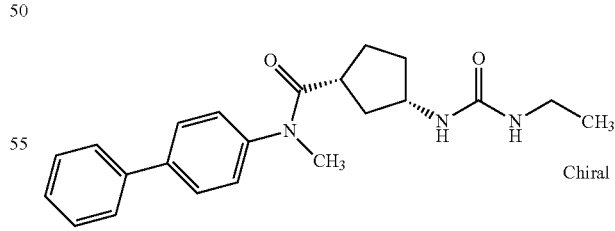

The compound is synthesised analogously to the method described above (example 1.1) with educt II.1 and ethyl isocyanate as educts.
Yield: 11.7 m g (71% of theory)
$C_{22}H_{27}N_3O_2$
EII Mass spectrum: m/z=366 [M+H]$^+$
ret. time: 2.23 min (HPLC method 4)

Example 3.5

(1R,3S)-3-(6-Dimethylamino-hexanoylamino)-cyclopentanecarboxylic acid N-biphenyl-4-yl-N-methyl-amide

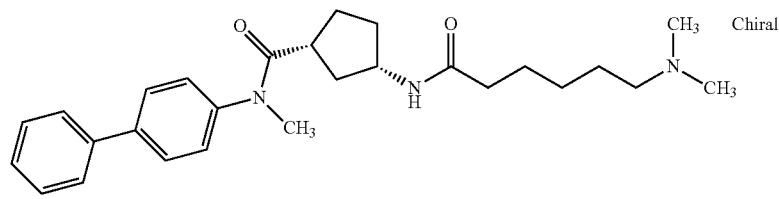 [SMILES: CN(C)CCCCCC(=O)N[C@H]1CC[C@@H](C(=O)N(C)c2ccc(-c3ccccc3)cc2)C1]

The compound is synthesised analogously to the method described above (example 1.4). with educt II.1 and 6-dimethylamino-hexanoic acid hydrobromide as educts.

Yield: 13.5 mg (55% of theory)

$C_{27}H_{37}N_3O_2$

EII Mass spectrum: m/z=436 [M+H]$^+$ ret. time: 1.69 min (HPLC method 2)

Example 4

Example 4.1

(1R,3S)-3-(3-Ethyl-ureido)-cyclopentanecarboxylic acid N-methyl-N-[4-(1-methyl-1H-benzoimidazol-2-yl)-phenyl]-amide

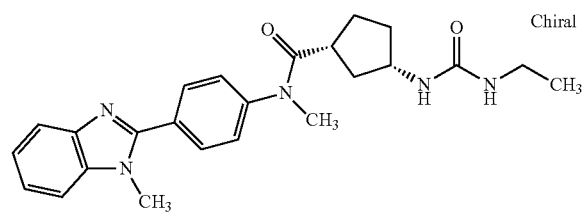 [SMILES: CCNC(=O)N[C@H]1CC[C@@H](C(=O)N(C)c2ccc(-c3nc4ccccc4n3C)cc2)C1]

The compound is synthesised analogously to the method described above (example 1.1) with educt III.1 and ethyl isocyanate as educts.

Yield: 11.6 mg (61% of theory)

$C_{24}H_{29}N_5O_2$

EII Mass spectrum: m/z=420 [M+H]$^+$ ret. time: 1.58 min (HPLC method 3)

Example 4.2

(1R,3S)-3-(6-Dimethylamino-hexanoylamino)-cyclopentanecarboxylic acid N-methyl-N-[4-(1-methyl-1H-benzoimidazol-2-yl)-phenyl]-amide

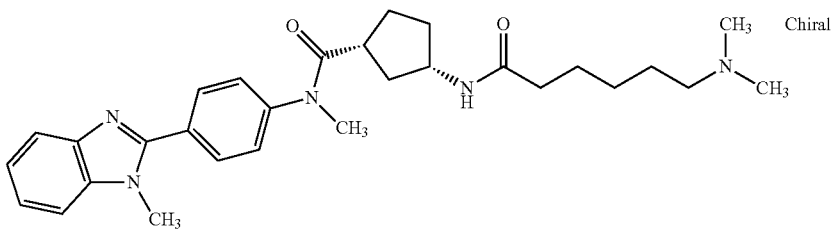 [SMILES: CN(C)CCCCCC(=O)N[C@H]1CC[C@@H](C(=O)N(C)c2ccc(-c3nc4ccccc4n3C)cc2)C1]

The compound is synthesised analogously to the method described above (example 1.4). Educt III.1 and 6-dimethylamino-hexanoic acid hydrobromide are used as educts.

Yield: 9.1 mg (34% of theory)

$C_{29}H_{39}N_5O_2$

EII Mass spectrum: m/z=490 [M+H]$^+$ ret. time: 1.25 min (HPLC method 2)

Example 5

Example 5.1

(1R,3S)-3-Propionylamino-cyclopentanecarboxylic acid N-methyl-N-[4-(1-methyl-1H-benzoimidazol-2-yl)-phenyl]-amide

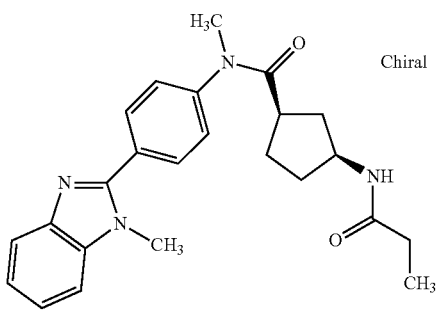 [SMILES: CCC(=O)N[C@H]1CC[C@@H](C(=O)N(C)c2ccc(-c3nc4ccccc4n3C)cc2)C1]

100.0 mg (0.54 mmol) (1R,3S)-3-Propionylamino-cyclopentanecarboxylic acid (educt IV.1) and 78.6 μL (0.59 mmol) 1-chloro-N,N,2-trimethyl-propenylamine are stirred in 5 mL dry THF at RT for 1 hour. Then this mixture is given to a mixture of 128.1 mg (0.54 mmol) N-methyl-N-[4-(1-methyl-1H-benzoimidazol-2-yl)-phenyl]-amine (educt III.1.a) and 107.0 μL (0.81 mmol) 2,4,6-collidine in DCM at RT. The mixture is stirred over night. The solvent is evaporated. The residue is taken up with water and extracted with DCM. The organic phase is dried and the solvent is evaporated. The residue is triturated with diethyl ether, filtered off and dried.

Yield: 136.0 mg (62% of theory)

$C_{24}H_{28}N_4O_2$

EII Mass spectrum: m/z=405 [M+H]$^+$ ret. time: 1.38 min (HPLC method 4)

Example 5.2

(1R,3S)-3-Propionylamino-cyclopentanecarboxylic acid N-[4-(imidazo[1,2-a]pyridin-2-yl)-phenyl]-N-methyl-amide

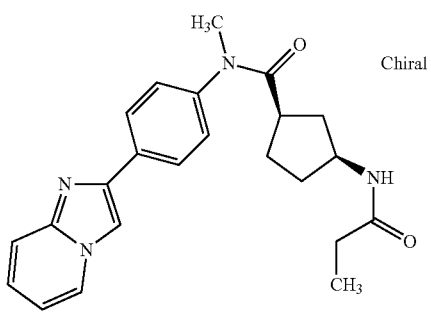 [SMILES: CCC(=O)N[C@H]1CC[C@@H](C(=O)N(C)c2ccc(-c3cn4ccccc4n3)cc2)C1]

The compound is synthesised analogously to the method described above (example 5.1) with educt IV.1 and educt IV.2 as educts.

Yield: 8.0 mg (13% of theory)

$C_{23}H_{26}N_4O_2$

EII Mass spectrum: m/z=391 [M+H]$^+$

Examples of Formulations

The following examples of formulations, which may be obtained analogously to methods known in the art, serve to illustrate the present invention more fully without restricting it to the contents of these examples. The term "active substance" denotes one or more compounds according to the invention, including the salts thereof.

Example 1

Dry Ampoule Containing 75 mg of Active Substance Per 10 ml

Composition:

| | |
|---|---|
| Active substance | 75.0 mg |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

Example 2

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried. To produce the solution ready for use, the product is dissolved in water for injections.

Example 3

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

Example 4

Tablet Containing 350 mg of Active Substance

Preparation:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example 5

Capsules Containing 50 mg of Active Substance

Composition:

| | | |
|---|---|---|
| (1) Active substance | 50.0 mg | |
| (2) Dried maize starch | 58.0 mg | |
| (3) Powdered lactose | 50.0 mg | |
| (4) Magnesium stearate | 2.0 mg | |
| | 160.0 mg | |

Preparation:

(1) is triturated with (3). This trituration is added to the mixture of (2) and (4) with vigorous mixing. This powder mixture is packed into size 3 hard gelatin capsules in a capsule filling machine.

Example 6

Capsules Containing 350 mg of Active Substance

Composition:

| | | |
|---|---|---|
| (1) Active substance | 350.0 mg | |
| (2) Dried maize starch | 46.0 mg | |
| (3) Powdered lactose | 30.0 mg | |
| (4) Magnesium stearate | 4.0 mg | |
| | 430.0 mg | |

Preparation:

(1) is triturated with (3). This trituration is added to the mixture of (2) and (4) with vigorous mixing. This powder mixture is packed into size 0 hard gelatin capsules in a capsule filling machine.

The invention claimed is:

1. A compound of formula I

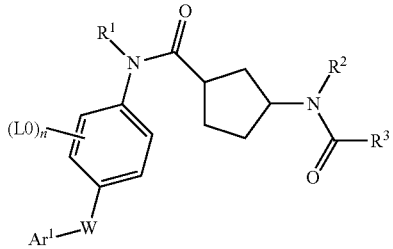

I wherein
$Ar^1$ denotes a phenyl ring or a 5- or 6-membered monocyclic heteroaryl-group which has 1 to 4 heteroatoms independently selected from the group consisting of N, O and S; and
wherein said phenyl ring or said 5- or 6-membered monocyclic heteroaryl-group may be linked to a group $Ar^2$ via a single bond or may be condensed to a group $Ar^2$,
wherein one or more C-atoms in the group $Ar^1$, including any group $Ar^2$, may be substituted independently of one another with a substituent L1; and
wherein one or more imino-groups in the group $Ar^1$, including any group $Ar^2$, may be substituted independently of one another with a substituent $R^{N0}$; and
$Ar^2$ denotes a 5- or 6-membered saturated or unsaturated carbocyclic ring which may have 1 or 2 heteroatoms independently selected from the group consisting of N, O and S, or may have 3 or 4 N-atoms; and
W denotes a single bond, —C≡C—, —CH=CH—, —CH$_2$—CH$_2$— or —CH$_2$—O—;
$R^1$ denotes $C_{1-4}$-alkyl;
$R^2$ denotes H or $C_{1-4}$-alkyl;
$R^3$ denotes $C_{1-6}$-alkyl, $C_{3-6}$-alkenyl, $C_{3-6}$-alkynyl, $C_{3-6}$-cycloalkyl or $R^{N1}R^{N2}N$—, wherein each of said alkyl, alkenyl, alkynyl and cycloalkyl groups may be substituted with one or more substituents selected from the group consisting of $R^{N1}R^{N2}N$—, $C_{1-4}$-alkyl-O—C(=O)—$R^{N0}N$—, HO—, $C_{1-4}$-alkyloxy, $C_{3-7}$-cycloalkyl, phenyl and pyridinyl,
wherein each of said cycloalkyl, said phenyl and said pyridinyl may be substituted with one or more substituents L2;
$R^{N0}$ denotes H or $C_{1-4}$-alkyl;
$R^{N1}$ and $R^{N2}$ independently of each other are selected from H, $C_{1-4}$-alkyl, phenyl, pyridinyl, phenyl-$C_{1-3}$-alkyl, pyridinyl-$C_{1-3}$-alkyl or $R^{N1}$ and $R^{N2}$ are linked to each other to form with the N-atom of the $R^{N1}R^{N2}N$— group a heterocyclic ring selected from the group consisting of pyrrolidinyl, piperidinyl, morpholinyl, thiomorpholinyl, piperazinyl or 4-($C_{1-4}$-alkyl)-piperazinyl;
L0 and L1 independently of each other are selected from the group consisting of F, Cl, Br, cyano, OH, $C_{1-4}$-alkyl, $C_{2-4}$-alkenyl, $C_{1-4}$-alkyloxy, $C_{1-4}$-alkylcarbonyl, $R^{N1}R^{N2}N$—, $R^{N1}R^{N2}N$—$C_{1-3}$alkyl-, $R^{N1}R^{N2}N$—CO, $C_{1-4}$-alkyl-CO—NR$^{N0}$— and $C_{1-4}$-alkyl-SO$_2$—NR$^{N0}$—, wherein alkyl-groups may be mono- or polyfluorinated;
L2 independently of each other are selected from the group consisting of F, Cl, Br, cyano, OH, $C_{1-4}$-alkyl, $C_{1-4}$-alkyloxy, $R^{N1}R^{N2}N$—, $R^{N1}R^{N2}N$—$C_{1-3}$-alkyl-, wherein alkyl-groups may be mono- or polyfluorinated;
n denotes an integer from 0 to 4;
while, unless otherwise stated, the above-mentioned alkyl groups may be straight-chain or branched,
or a salt thereof.

2. A compound according to claim 1, of the formula I-RS:

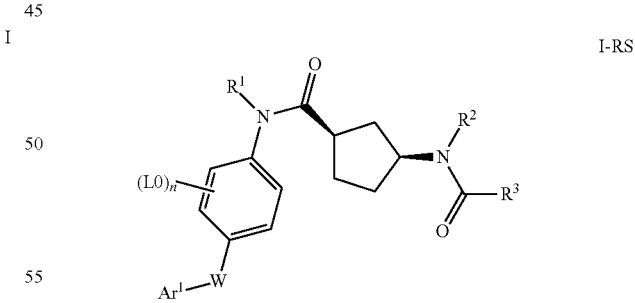

I-RS or a salt thereof.

3. A compound according to claim 1, wherein the group $R^1$ denotes methyl and the group $R^2$ denotes H, or a salt thereof.

4. A compound according to claim 1, wherein the group W denotes a single bond, or a salt thereof.

5. A compound according to claim 1, wherein the group $Ar^1$ denotes phenyl, thienyl, pyridinyl, pyrrolyl, imidazolyl, triazolyl, furanyl or oxazolyl, or a salt thereof.

6. A compound according to claim 1, wherein the group $Ar^1$ denotes phenyl, thienyl, pyridinyl, pyrrolyl, imidazolyl, triazolyl, furanyl, isoxazolyl or oxazolyl, all of which are condensed to a group $Ar^2$ wherein $Ar^2$ denotes phenyl, pyridyl, pyrrolyl, dihydropyrrolyl, furanyl, dihydrofuranyl or dioxolyl, or a salt thereof.

7. A compound according to claim 1, selected from the group consisting of:
- (1R,3S)-3-propionylamino-cyclopentanecarboxylic acid N-biphenyl-4-yl-N-methyl-amide,
- (1R,3S)-3-acetylamino-cyclopentanecarboxylic acid N-(4-benzooxazol-2-yl-phenyl)-N-methyl-amide, and
- (1R,3S)-3-propionylamino-cyclopentanecarboxylic acid N-(4-benzooxazol-2-yl-phenyl)-N-methyl-amide, or a tautomer or salt thereof.

8. A physiologically acceptable salt of a compound of the formula I according to claim 1.

9. A pharmaceutical composition comprising one or more compounds according to claim 1, or a physiologically acceptable salt thereof, together with one or more inert carriers and/or diluents.

10. A method for treating obesity in a patient in need thereof wherein a compound of formula I according to claim 1 or a physiologically acceptable salt thereof is administered to the patient.

* * * * *